United States Patent
Lomnitz et al.

(10) Patent No.: US 10,545,107 B2
(45) Date of Patent: Jan. 28, 2020

(54) SYSTEM, DEVICE AND METHODS FOR MEASURING SUBSTANCES' DIELECTRIC PROPERTIES USING MICROWAVE SENSORS

(71) Applicant: VAYYAR IMAGING LTD, Yehud (IL)

(72) Inventors: Yuval Lomnitz, Herzlia (IL); Jonathan Rosenfeld, Ramat hasharon (IL); Doron Cohen, Tel-Aviv (IL); Shachar Shayovitz, Ness Ziona (IL)

(73) Assignee: VAYYAR IMAGING LTD, Yehud (IL)

( * ) Notice: Subject to any disclaimer, the term of this patent is extended or adjusted under 35 U.S.C. 154(b) by 0 days.

(21) Appl. No.: 15/569,485

(22) PCT Filed: Apr. 26, 2016

(86) PCT No.: PCT/IL2016/050440
§ 371 (c)(1),
(2) Date: Oct. 26, 2017

(87) PCT Pub. No.: WO2016/174675
PCT Pub. Date: Nov. 3, 2016

(65) Prior Publication Data
US 2018/0299394 A1    Oct. 18, 2018

Related U.S. Application Data

(60) Provisional application No. 62/152,928, filed on Apr. 26, 2015.

(51) Int. Cl.
*G01R 15/00* (2006.01)
*G01N 27/02* (2006.01)
*G01N 22/02* (2006.01)

(52) U.S. Cl.
CPC ........... *G01N 27/025* (2013.01); *G01N 22/02* (2013.01)

(58) Field of Classification Search
None
See application file for complete search history.

(56) References Cited

U.S. PATENT DOCUMENTS 2,735,070 A    2/1956  Riblet
4,010,715 A    3/1977  Robar et al.
(Continued)

FOREIGN PATENT DOCUMENTS

EP    1845364 A2    10/2007
WO    2014/080360 A2    5/2014

OTHER PUBLICATIONS

Yan Pailhas et al., "Synthetic Aperture Imaging and Autofocus With Coherent MIMO Sonar Systems", http://osl.eps.bw.ac.uk/files/uploads/publications/SASSARconf_Pailhas.pdf (2014).
(Continued)

*Primary Examiner* — Aditya S Bhat
(74) *Attorney, Agent, or Firm* — Browdy and Neimark, PLLC

(57) ABSTRACT

Systems, device and methods are provided for measuring parameters of a medium such as the dielectric properties of a medium including a plurality of layers, using an array of sensors. The array comprises at least two transducers and at least one transceiver attached to said at least two transducers, the at least one transceiver is configured to transmit at least one signal toward the medium and receive a plurality of signals affected by the medium; a data acquisition unit and at least one processor unit, configured to: process the affected plurality of signals to yield a plurality of transfer functions wherein each of said plurality of transfer functions comprising said medium response between two transducers of said at least two transducers as function of frequency or time; and process the plurality of transfer functions to yield
(Continued)

a plurality of statistical measures, and process said statistical measures to calculate said medium parameters.

8 Claims, 14 Drawing Sheets

(56) References Cited

U.S. PATENT DOCUMENTS

| | | | |
|---|---|---|---|
| 4,060,833 A * | 11/1977 | Onyshkevych | H03H 9/0285 348/725 |
| 4,211,224 A | 7/1980 | Kubach | |
| 4,211,911 A | 7/1980 | Dehn | |
| 4,626,805 A | 12/1986 | Jones | |
| 5,039,824 A | 8/1991 | Takashima | |
| 5,101,163 A | 3/1992 | Agar | |
| 5,389,735 A | 2/1995 | Bockelman | |
| 5,572,160 A | 11/1996 | Wadell | |
| 5,583,510 A | 12/1996 | Ponnapalli | |
| 5,718,208 A | 2/1998 | Brautigan | |
| 5,774,801 A | 6/1998 | Li et al. | |
| 5,829,522 A | 11/1998 | Ross | |
| 6,636,816 B1 | 10/2003 | Dvorak et al. | |
| 7,034,548 B2 | 4/2006 | Anderson et al. | |
| 7,148,702 B2 | 12/2006 | Wong et al. | |
| 7,387,010 B2 | 6/2008 | Sunshine | |
| 7,448,880 B2 | 11/2008 | Osaka | |
| 7,668,046 B2 | 2/2010 | Banker | |
| 7,755,010 B2 | 7/2010 | Godshalk | |
| 8,050,740 B2 | 11/2011 | Davis | |
| 8,095,204 B2 | 1/2012 | Smith | |
| 8,494,615 B2 | 7/2013 | Melamed et al. | |
| 8,620,238 B2 | 12/2013 | Chan et al. | |
| 2002/0165295 A1 | 11/2002 | Matsumoto | |
| 2003/0115232 A1 | 6/2003 | Lipp | |
| 2003/0146767 A1 | 8/2003 | Steele | |
| 2004/0077943 A1 | 4/2004 | Meaney | |
| 2004/0190377 A1 | 9/2004 | Lewandowski | |
| 2005/0040832 A1 | 2/2005 | Steele et al. | |
| 2005/0255276 A1 | 11/2005 | Bethune | |
| 2006/0034726 A1 | 2/2006 | Sunshine et al. | |
| 2006/0176062 A1 | 8/2006 | Yang et al. | |
| 2006/0220658 A1 | 10/2006 | Okamura | |
| 2008/0296306 A1 | 12/2008 | Handa | |
| 2011/0060215 A1 | 3/2011 | Tupin | |
| 2011/0068807 A1 | 3/2011 | Kesil et al. | |
| 2011/0098972 A1 | 4/2011 | Chen et al. | |
| 2011/0134001 A1 | 6/2011 | Sakata | |
| 2012/0242341 A1 | 9/2012 | Olsson | |
| 2012/0327666 A1 | 12/2012 | Liu | |
| 2013/0141287 A1 | 6/2013 | Pallonen | |
| 2013/0231046 A1 | 9/2013 | Pope | |
| 2013/0241780 A1 | 9/2013 | Amm et al. | |
| 2013/0271328 A1 | 10/2013 | Nickel | |
| 2013/0300573 A1 | 11/2013 | Brown | |
| 2013/0329139 A1 | 12/2013 | Feher | |
| 2014/0066757 A1 | 3/2014 | Chayat | |
| 2014/0179239 A1 | 6/2014 | Nickel | |
| 2014/0278445 A1 | 9/2014 | Eddington, Jr. et al. | |
| 2015/0097579 A1 | 4/2015 | Sharma et al. | |
| 2016/0336643 A1 | 11/2016 | Pascolini | |

OTHER PUBLICATIONS

Fineup, J., "Synthetic-aperture radar autofocus by maximizing sharpness", http://www.opties_rochester.edu/workgroups/fineup/PUBLICATIONS/OL00_SARFocMaxSharp.pdf (2000).

Bates, James Stewart, "Expansions and Discussions of the Phase Gradient Algorithm", http://digitalcommons.usu.edu/cgi/viewcontent.cgi?article=1320&context=spacegrant (1998).

R. Streich et al., "Accurate imaging of multicomponent GPR data based on exact radiation patterns," IEEE Transactions on Geoscience and Remote Sensing, vol. 45, 93-103 (2007).

Crocco L et al: "Early-stage leaking 1-13 pipes GPR monitoring via microwave A tomographic inversion" Journal of Applied Geophysics. Elsevier. Amsterdam. NL. vol. 67. No. 4. Apr. 1, 2009 (Apr. 1, 2009). pp. 270-277. XP026033856.

Ayliffe et al., 'Electric Impedance Spectroscopy' Using Microchannels with Integrated Metal Electrodes' IEEE Journal of Microelectromechanical Systems, vol. 8, No. 1, Mar. 1999.

P. Lombardini et al., "Criteria for the Design of Loop-Type 12 Directional Couplers for the L Band" (1956).

Pallavi R. Malamel et al., "Microwave Reflectometry Based Electrical Characterization of Milk for Adulteration Detection", Advance in Electronic and Electric Engineering, ISSN 2231-1297, vol. 4, No. 5 (2014), pp. 487-492.

Valerie Favry, "Design and Development of a Novel Electronic Sensor for Detecting Mastitis Based on Conductance/Impedance Measurements", Thesis submitted for the Degree o f Master o f Science,Supervised by Prof. Dermot Diamond School o f Chemical Sciences, National centre for Sensor Research Jul. 2004.

Ali F. Yegulap et al., "Minimum Entropy SAR Autofocus", http://www.ll.mit.edu/asap/asap_99/abstract/Yegulap.pdf (1999).

David Atkins et al., "Motion Correction", ISMRM 2011 Montreal Sunrise Course: Image Reconstruction (2011).

Gary F. Margrave et al., "Full Waveform Inversion Using One-way Migration and Well Calibration", IEEE Transactions on Antennas and Propagation, vol. 54, No. 11, Nov. 2006.

David Winters, "Estimation of the Frequency-Dependent Average Dielectric Properties of Breast Tissue Using a Time-Domain Inverse Scattering Technique", IEEE Transactions on Antennas and Propagation, vol. 54, No. 11, Nov. 2006.

Bjorn Engquist et al., "Application of the Wasserstein Metric to Seismic Signals", Communications in Mathematical Sciences, Nov. 2013.

D. Wahl et al., "Phase Gradient Autofocus—A Robust Tool for High Resolution SAR Phase Correction", IEEE Transactions on Aerospace and Electronic Systems vol. 30, No. 3 Jul. 1994.

* cited by examiner

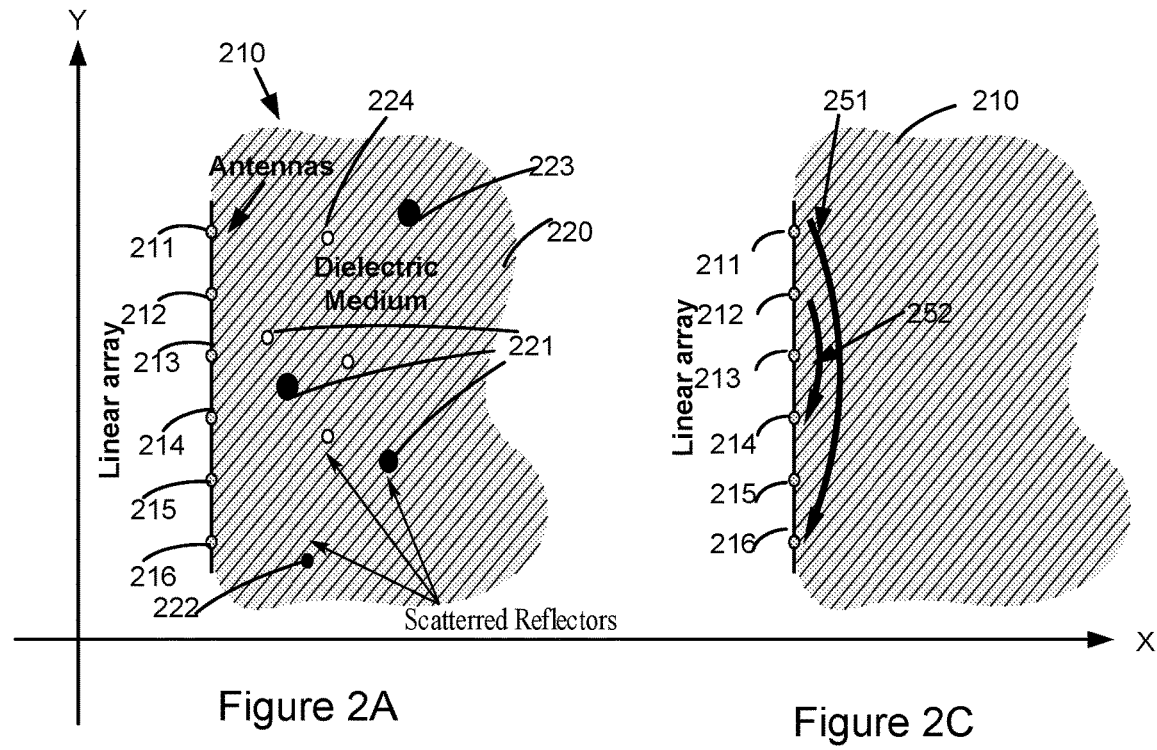
Figure 2A
Figure 2C
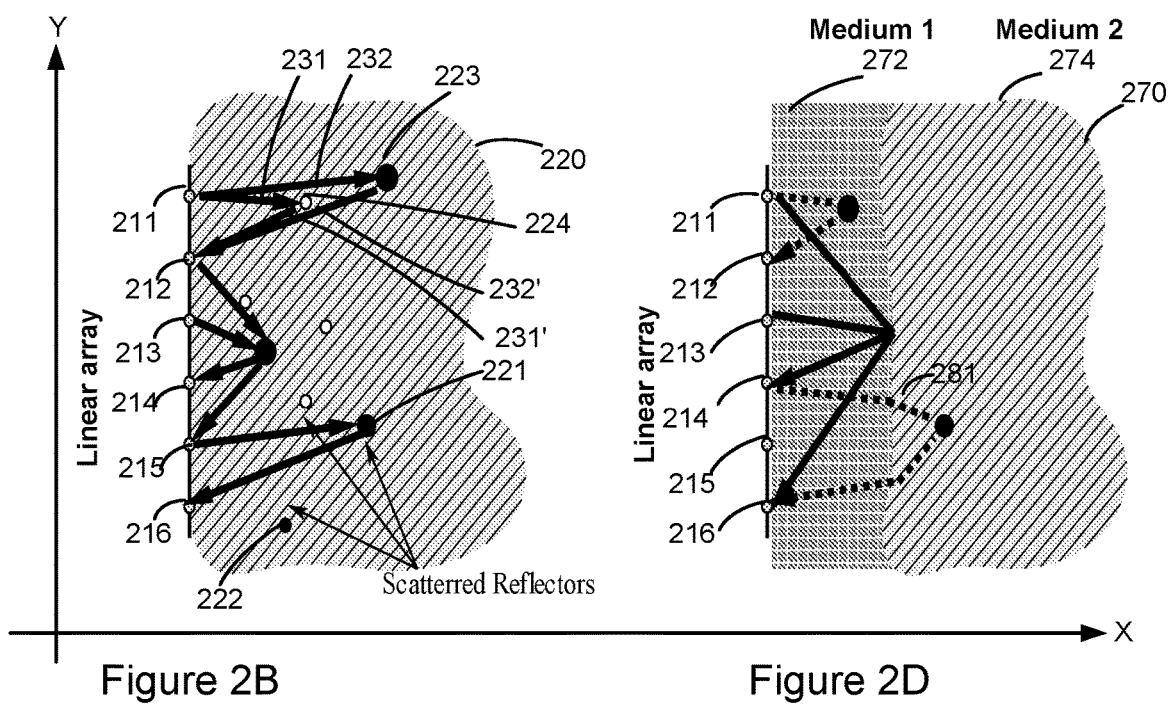
Figure 2B
Figure 2D

SYSTEM, DEVICE AND METHODS FOR MEASURING SUBSTANCES' DIELECTRIC PROPERTIES USING MICROWAVE SENSORS

CROSS-REFERENCE

The present application claims the benefit of U.S. Provisional Application Ser. No. 62/152,928, filed on Apr. 26, 2015, entitled "SYSTEM DEVISE AND METHOD FOR ESTIMATING DIELECTRIC MEDIA PARAMETERS", the entire disclosures of which are incorporated herein by reference. The subject matter of the present application is related to PCT Application PCT/IL2015/050126, filed Feb. 4, 2015, entitled "SYSTEM DEVISE AND METHOD FORTESTING AN OBJECT", PCT Application PCT/IL2015/050099, filed on Jan. 28, 2015, entitled "SENSORS FOR A PORTABLE DEVICE", U.S. application Ser. No. 14/605,084, filed on Jan. 26, 2015 entitled "VECTOR NETWORK ANALYZER" U.S. application Ser. No. 14/499,505, filed on Sep. 30, 2015 entitled "DEVICE AND METHOD FOR CALIBRATING ANTENNA ARRAY SYSTEMS" U.S. application Ser. No. 14/69,681, filed on Apr. 27, 2015 entitled "PRINTED ANTENNA HAVING NON-UNIFORM LAYERS" each of which is incorporated herein by reference in its entirety.

FIELD OF THE INVENTION

The present invention relates to a sensing system device and method for measuring the dielectric properties of one or more substances or objects and more specifically, but not exclusively, to sensing substances located in a homogenous or inhomogeneous media using Radio Frequency (RF) sensors such as microwave sensors.

BACKGROUND OF THE INVENTION

Prior to the background of the invention being set forth, it may be helpful to set forth definitions of certain terms that will be used hereinafter.

The term 'media' or 'medium' as used herein is defined as material(s), subject(s) or object(s) such as an homogeneous or close to homogenous material in which scaterrers may be present in and may be for example air, concrete, plaster, fluids human tissues etc.

The term '$\epsilon\_R$' (relative permittivity), refraction index (n), and propagation velocity (denoted v) as used herein and through the specification and claims should be used interchangeably, since in non-ferromagnetic materials they are related by the Eq $v=c/n$, $n=\sqrt{(\epsilon\_R)}$, where c is the speed of light. However this is merely a convenience which does not limit the scope of the invention.

The term 'velocity factor' (hereinafter wave propagation speed or velocity of propagation (VoP or v_P) of a transmission medium as used herein and through the specification and claims is the ratio of the speed at which a wavefront (of an acoustic signal, for example, or an electromagnetic signal, a radio signal, a light pulse in a fibre channel or a change of the electrical voltage on a copper wire) passes through the medium, to the speed of light in a vacuum. For optical signals, the velocity factor is the reciprocal of the refractive index.

The term 'reflector' or scattering object herein and through the specification and claims should be defined as any object reflecting all or part of the incident (e.g. electromagnetic) wave. The detection or imaging of objects through media is a challenging task which requires advanced and sophisticated electronic imaging systems. The media may be defined as Known methods and systems of imaging such as confocal imaging of reflective targets in homogenous or layered media using a set of active measurements such as antenna array and/or SAR (Synthetic Aperture Radar) scanning requires prior knowledge of the media parameters. Primarily the major parameter which must be known is a propagation velocity (associated with the reflective index or dielectric permittivity) in order to back-propagate and focus all reflections from a given target at the same point.

Other media parameters, such as loss (attenuation, e.g. due to conductivity) and dispersion (i.e. varying parameters over frequency) are also important for imaging and have to be estimated. For example, knowledge of the loss parameters is important in order to scale received signals correctly, and distinguish targets which have a weak reflection from those who suffered significant path loss.

Knowledge of the media parameters may be important on its own and not only as a parameter for imaging; for example, characterization of the material(s) of which a wall is made, or properties of fluid in a pipe.

Furthermore, the media can be non-homogenous but in a way that enables the identification of homogenous regions. The most pertinent example is layered media where the layers extend in the directions parallel to the array. For example a layer of stucco followed by concrete (where dielectric parameters and layer depth are unknown and need to be estimated).

In the field of SAR there are a number of known solutions for estimation of unknown parameters, via autofocusing of the resulting image, for example as illustrated in an article titled "SYNTHETIC APERTURE IMAGING AND AUTOFOCUS WITH COHERENT MIMO SONAR SYSTEMS" by Yan Pailhas and Yvan Petillot, OSL, Heriot Watt University, Edinburgh, UK and in article titled "Synthetic-aperture radar autofocus by maximizing sharpness" by J. R. Fienup (Feb. 15, 2000/Vol. 25, No. 4/OPTICS LETTERS) Yvan Petillot, [Yegulalp 1999], [Fienup 2000])).

In the case of SAR, in the context of large distances (kilometers) where the interface is air (non dielectric) the main effort of autofocusing is to correct errors in the antenna locations. As opposed to solutions based on the image itself, PGA (phase gradient autofocus) utilizes the measurements in a more direct fashion (for example as illustrated in the article: "EXPANSIONS AND DISCUSSIONS OF THE PHASE GRADIENT ALGORITHM" by James Stewart Bates [D. Wahl]), to solve the same problem. Some authors suggest using autofocus algorithms to estimate and correct the target velocity (not the propagation velocity) as for example illustrated in an article titled "SYNTHETIC APERTURE IMAGING AND AUTOFOCUS WITH COHERENT MIMO SONAR SYSTEMS" by Yan Pailhas and Yvan Petillot and also in article titled: "Retrospective Motion Correction" by David Atkinson.

Estimation of media velocity may be found in respect to sonar applications. Mainly, estimation of media velocity found in literature is treated as an inverse problem, i.e. the aim is to find a full characterization of a possibly inhomogenous medium which would have produced reflected signals close to the ones measured. An example of such solution may be found in an article titled: "Full Waveform Inversion Using One-way Migration and Well Calibration" by Gary F. Margrave, Robert J. Ferguson, and Chad M. Hogan and in article titled "Estimation of the Frequency-Dependent Average Dielectric Properties of Breast Tissue Using a Time-Domain Inverse Scattering Technique" by David W. Winters).

In the field of seismic measuring, seismic signals are typically compared using travel time difference or L2 difference. According to prior art solutions a Wasserstein metric provided is as an alternative measure of fidelity or misfit in seismology. The numerical computation is based on fast numerical methods for the Monge-Amp'ere equation and optimal transport. An example of such solution may be found in an article titled: 'APPLICATION OF THE WASSERSTEIN METRIC TO SEISMIC SIGNALS' by BJORN ENGQUIST and BRITTANY D. FROESE.

SUMMARY OF INVENTION

According to a first aspect of the invention there is provided a system for measuring parameters of a medium, the system comprising: an array, the array comprises at least two transducers, wherein at least one of said at least two transducers is configured to transmit a signal towards said medium, and at least one transceiver attached to said at least two transducers, the at least one transceiver is configured to transmit at least one signal toward the medium and receive a plurality of signals affected by the medium; a data acquisition unit configured to receive and store said affected plurality of signals; and at least one processor unit, said at least one processor unit is configured to:
(a) process said affected plurality of signals to yield a plurality of transfer functions wherein each of said plurality of transfer functions comprising said medium response between two transducers of said at least two transducers as function of frequency or time;
(b) process said plurality of transfer functions to yield a plurality of statistical measures, wherein each of said statistical measures, is calculated from at least two transfer functions of said plurality of transfer functions; and
(c) process said statistical measures to calculate said medium parameters.

In an embodiment, each of said plurality of statistical measures, is calculated from at least one pair of said plurality of transfer functions by multiplying a scalar function of a first transfer function by a scalar function of a second transfer function, and averaging the result of said multiplication over multiple pairs of transfer functions.

In an embodiment, each statistical measure of said plurality of statistical measures is an empirical covariance ($\Lambda_y$) of pairs of said transfer functions, wherein each transfer function of said at least two transfer functions is represented as a vector of samples, and the covariance between two vectors of samples is calculated over a plurality of pairs of said transfer functions having the same configuration.

In an embodiment, the system further comprises:
(a) providing a model, the model comprises a theoretical covariance matrix ($\Lambda_\theta$) for every value of the medium parameters $\theta$.
(b) comparing said theoretical covariance matrix to an empirical covariance matrix produced from the plurality of signals, using a comparison metric $\mu$.
(c) selecting a value of the parameters $\theta$ that maximizes a comparison metric $\mu(\Lambda_\theta, \Lambda_y)$ as an estimate of the medium parameters $\theta$.

In an embodiment, the comparison metric $\mu(\Lambda_\theta, \Lambda_y)$ is selected from the group comprising of:

$$\mu_1(y;\theta)=c(\theta)\cdot tr(\Lambda_\theta \Lambda_y), \mu_2(y;\theta)=c(\theta)\cdot tr(\Lambda_\theta^{-1} \Lambda_y)$$
$$,\mu_3(y;\theta)=c(\theta)\cdot tr((\Lambda_\theta+\lambda I)^{-1}\Lambda_y),$$

wherein $c(\theta)$ is a normalization function independent of the measurements y.

In an embodiment, the parameters are selected from the group comprising of: a propagation velocity, dielectric constant ($\epsilon_R$), refraction index (n).

In an embodiment, an estimation of the propagation velocity of said medium comprises:
(a) calculating a plurality of tangent lines for at least one couple of transfer functions, said plurality of tangent lines representing a geometrical region in space, said region comprising ellipsoids, wherein each of said ellipsoids is defined by a constant sum of distances from said at least two transducers, such that said ellipsoids of the two couples of pairs of transducers are tangential at each point on the tangent lines;
(b) translating the sum of distances associated with the tangent lines to time delays, for each hypothesis on the propagation velocity;
(c) integrating the empirical covariance matrix over said time delays for each hypothesis on the propagation velocity;
(d) selecting a propagation velocity for which said integration yields the maximum result.

In an embodiment, the empirical covariance matrix is normalized before integrating the empirical covariance matrix.

In an embodiment, the normalization comprises dividing each element (i,j) in the covariance matrix by the square root of the product of elements (i,i) and (j,j).

In an embodiment, integrating the empirical covariance matrix is performed separately over distinct ranges of times or distances of said medium, said distinct ranges are defined by at least one section of the tangent lines, to produce an estimate of propagation velocity per a distinct range of depths in the medium.

According to a second aspect of the invention there is provided a system for measuring parameters of a medium, the system comprising: an array, the array comprises at least three transducers, wherein at least two transducers of said at least three transducers are configured to transmit a signal towards said medium, and a transceiver attached to said at least three transducers said array is configured to transmit at least one signal towards the medium and receive a plurality of signals affected by the medium; a data acquisition unit configured to receive and store said plurality of affected signals; and at least one processor unit, said at least one processor unit is configured to:
(a) process said plurality of affected signals to yield a plurality of transfer functions wherein each of said plurality of transfer functions comprising the medium response between the at least two transducers as function of frequency or time, and
(b) comparing said plurality of affected signals that have travelled different path lengths within the medium according to said plurality of transfer functions to yield said medium parameters.

In an embodiment, the medium parameters comprise a propagation velocity in the medium, or a dielectric constant of the medium.

In an embodiment, the at least three transducers are RF antennas, said RF antennas having a distance therein.

In an embodiment, the system comprising cross correlating time domain of said plurality of transfer functions of antenna pairs of said RF antennas, said antenna pairs having different distances between them.

In an embodiment, the system comprising conjugate-multiplying frequency domain of said transfer functions of antenna pairs of said RF antennas wherein said antenna pairs having different distances to yield said medium parameters.

In an embodiment, the system further comprising
(a) finding for at least one transfer function of said plurality of transfer functions a reference transfer function such that said RF antennas configurations of the at least one transfer function and the reference transfer functions are similar and the distance between said the at least one transfer function and the reference transfer functions is different;
(b) performing cross correlation of the at least one transfer functions in time domain representation with the reference transfer functions;
(c) converting the cross correlation results from time domain to an indicator function in hypothetic velocity domain by using a conversion X'(v)=X(t)
where:
X(t) is the cross correlation result, $$t = \frac{\Delta D}{v}$$

and ΔD is the difference in said RF antennas distance between two antenna pairs of said RF antennas; and
(d) combining an indicator functions X'(v) for said plurality of transfer functions and finding a peak of said plurality of transfer functions to yield an estimation of velocity v of said medium.

In an embodiment, the system comprising further comprising:
(a) separating the plurality of transfer functions into a plurality of sets termed configurations, and further separating each set of said plurality of sets according to the distances between the RF antennas;
(b) calculating a metric $\mu(Y;\theta)=\Sigma_{f,c}|\Sigma_d Y(f,d,c) \cdot P^*_\theta(f,d) \cdot w_1(d,c)|^2 \cdot w_2(f,c)$ for each value of a parameter θ where:
Y(f,d,c) is a signal at a frequency f and antenna distance d of said pairs of antennas with configuration c, and $P_\theta$(f,d) is a path model for a given frequency and distance given a parameter θ said parameter θ is a scalar or vector, and $w_1, w_2$ are non-negative weighing functions of choice.
(c) finding a value of said medium parameter vector θ that maximizes the metric μ(Y;θ).

In an embodiment, said medium parameters comprise a propagation velocity v.

In an embodiment, the metric is $\mu(Y;v)=\Sigma_{f,c}|\Sigma_d Y(f,d,c) \cdot e^{j2\pi f/v \cdot d} \cdot w_1(d,c)|^2 \cdot w_2(f,c)$ According to a third aspect of the invention there is provided a system for measuring parameters of a medium, the system comprising:
an array, the array comprises at least three transducers, wherein at least one transducer of said at least three transducers is configured to transmit a signal towards said medium, and at least one transceiver attached to said at least three transducers said array is configured to transmit at least one signal towards the medium and receive a plurality of signals affected by the medium; a data acquisition unit configured to receive and store said plurality of affected signals; and at least one processor unit, said at least one processor unit is configured to:
(a) process said plurality of reflected signals to yield a plurality of transfer functions wherein each of said plurality of transfer functions comprises said medium response between said at least two transducers as function of frequency or time, and (b) process said plurality of transfer functions to yield an estimate of a depth of at least one layer of said medium, or verifying the existence of layers in said medium, by comparing said plurality of affected signals that have travelled different lengths within the medium.

In an embodiment the plurality of transfer functions are converted to time domain and wherein the processing of said plurality of transfer functions further comprises: calculating a propagation time ($T_p(\theta)$) from each pair of transducers of said at least three transducers to the at least one layer of said medium, according to a plurality of hypotheses θ on at least one layer parameters, where p is a pair of transducers or transfer function index.

In an embodiment the system further comprises: combining the parameters to yield a fit metric S(θ); and finding the value of the parameters θ that maximizes said fit metric S(θ).

In an embodiment the system further comprises: identifying at least two layers of said medium by said at least one processing unit, said identification comprises:
(a) finding multiple peaks in a fit metric (S(θ), $\theta_1, \theta_2, \ldots$);
(b) arranging the at least two layers according to their order of distance from the array; and
(c) measuring the parameters of each layer of said at least two layers.

In an embodiment the system further comprises: compensating for each layer of said at least two layers parameters $\theta_i$ the effect of previous layers $\theta_1, \ldots \theta_{i-1}$ to obtain the parameters of each layer of said at least two layers.

In an embodiment the fit metric is obtained by an equation selected from the group comprising of:

$$S(\theta) = |\Sigma_p y_p(T_p)| \text{ or } S(\theta) = \max\{\Sigma_p(\max\{y_p(T_p), 0\})^2,$$
$$\Sigma_d(\min\{y_p(T_p), 0\})^2\}, \text{ or}$$
$$S(\theta) = |\hat{a}|\Sigma_p \min\left(\max\left(\frac{y_p(T_p)}{\hat{a}}, 0\right), 1\right) \text{ where}$$
$$\hat{a} = \text{median } (y_p(T_p)) \text{ or}$$
$$S(\theta) = \max_{q \in \{\pm 1\}} \Sigma_p \max(0, y_p(T_p) \cdot q).$$

In an embodiment, each layer v of said at least two layers is characterized by a width (w) and propagation velocity within said layer v v (θ=(w,v)), or dielectric constant, or refraction index.

In an embodiment, the propagation time of said at least two layers are calculated according to $$T_p(\theta) = \frac{2}{v}\sqrt{w^2 + \left(\frac{L_p}{2}\right)^2}$$

where $L_p$ is the distance between the at least two transducers.

In an embodiment, the medium is positioned in parallel to the array.

In an embodiment the system further comprises: (a) finding multiple peaks in the fit metric S(θ), $\theta_1, \theta_2, \ldots$ where $\theta_i=(w_i,v_i)$.
(b) arranging the layers of said medium according to their order of distance from the array $w_i$;
(c) compensating for each layer parameters which effect previous layers according to a relations: $\tilde{w}_i = w_i - w_{i-1}$ and $$\tilde{v}_i = \frac{w_i - w_{i-1}}{\frac{w_i}{v_i} - \frac{w_{i-1}}{v_{i-1}}};$$

and (d) characterizing each layer of said at least two layers according to said compensated parameters.

According to a forth aspect of the invention there is provided a system for measuring parameters of a medium or a target, the system comprising:

an array, the array comprises at least two transducers, where at least one transducer of said at least two transducers is configured to transmit a signal, and a transceiver attached to said at least two transducers, said transceiver is configured to transmit a plurality of signals towards the medium or the target and receive a plurality of signals affected by the medium or the target; a data acquisition unit configured to receive and store said plurality of affected signals; and at least one processor unit, said at least one processor unit is configured to:

(a) process said plurality of affected signals to yield a plurality of transfer functions each of said plurality of transfer functions comprises said medium or target response between said at least two transducers, as function of frequency or time; and (b) processing said plurality of transfer functions to yield an image (e.g. of targets in said medium), based on an initial assumption on the medium parameters ($\theta_0$);

(c) identify peaks in the image;

(d) obtain parameters $\theta$ of the medium or the target by maximizing said image peaks.

In an embodiment, the parameters $\theta$ is obtained according to the plurality of transfer functions and the image and does not require re-computing the image.

In an embodiment, maximizing said image peaks comprises:

(a) gradually changing the medium parameters compared to said medium parameters initial value ($\theta_0$);

(b) re-estimating the location of the image peak by calculating a plurality of images voxels at the vicinity of the previous peak location, and providing a new location based on the image voxels values, following each change in the parameters.

In an embodiment, the medium parameters are changed by increasing or decreasing the medium parameters values.

In an embodiment, maximizing peaks of the image comprises:

(a) deriving an approximate small-deviation model for each image peak at location $r_0$ at said medium, said model comprises a contribution of each of said plurality of transfer functions to the image, as a plane, wherein the plane parameters change linearly with the change of the parameters $\theta - \theta_0$ of the medium or target.

(b) solving a least-squares optimization function model that maximizes the sum of said contributions under an unknown variation of parameters $\theta - \theta_0$ and unknown new peak location r.

In an embodiment, the small deviation model comprises a plane in direction $d_p$ wherein $d_p$ is a normalized vector passing through a point $r_0 + d_p \cdot g_p \alpha$ where $g_p$ is a shift gradient and $\alpha$ determines the relative change in propagation velocity.

In an embodiment, wherein the approximate small-deviation model comprises $$g_p = \frac{L}{\|d_T + d_R\|}$$

where L is the total path distance in the medium and $d_T$, $d_R$ are the directions of arrival and departure from the point $r_0$ in space to the at least two transducers.

In an embodiment, the system further comprising estimating as error $\alpha$ in propagation velocity, wherein $\alpha$ is the ratio of true velocity and the velocity assumed for imaging the medium, is $$\hat{\alpha} = \left(\sum_p A_p \cdot \begin{bmatrix} d_p d_p^T & d_p g_p \\ d_p^T g_p & g_p^2 \end{bmatrix} + \lambda I\right)^{-1} \sum_p g_p A_p (r_0^T d_p)$$

where $A_p$ is a contribution of each transfer function of antenna pair p to the image intensity.

In an embodiment, the image intensity for a plurality of image peaks is computed, each of said image peaks intensity is presented as a quadratic expression in a change parameter $\alpha$, as $I(\alpha) = I_0 - 2\beta D_1 \alpha - D_2 \beta \alpha^2$ and the parameter $\alpha$ is selected such that it maximizes a metric computed over the plurality of peak values $I(\alpha)$, wherein said metric may be a sum, max, $L_p$ norm, or percentile.

According to a fifth aspect of the invention there is provided a system for measuring parameters of a medium, the system comprising: an array of conductive elements, the array comprises at least two sensors, wherein each of said at least two sensors comprises at least one conductive element and wherein each sensor of said at least two sensors is connected to a transceiver, said transceiver is configured to transmit and/or receive an RF signal; a data acquisition unit configured to transmit sensing signals at radio frequencies, measure and store an impedance measurements at one or more transmit ports of said at least two sensors and receive and store the received signals at receive ports of said at least two sensors; and at least one processor unit, said at least one processing unit is configured to process said measurements and estimate the medium parameters at a plurality of depths or at a plurality of locations along the medium surface, by comparing the reflected RF responses of sensors, at same location or same effective location.

In an embodiment the at least two sensor have different physical sizes.

In an embodiment the at least two sensors are concentric sensors or positioned side by side.

In an embodiment the system further comprises moving said at least two sensors following each measurement of said medium.

In an embodiment each sensor of said at least two sensors comprises at least two conductive elements.

In an embodiment the conductive elements are fed differentially by introducing a voltage or current to the said conductive elements with inverse signs.

In an embodiment the transducers are antennas.

In an embodiment the array is a Radio Frequency (RF) array and the at least two transducers are RF antennas configured to transmit an RF signal.

In an embodiment the plurality of signals are radio frequency (RF) signals.

In an embodiment the plurality signals are selected from the group comprising of: pulses signals, stepped/swept frequency signals.

In an embodiment the plurality of signals bandwidth is within the UWB (3-10 Ghz) range or signals in the range between 1 Ghz and 100 Ghz.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks, according to embodiments of the invention, could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein, are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The subject matter disclosed may best be understood by reference to the following detailed description when read with the accompanying drawings in which:

FIGS. 2A-2D are schematic views of various scenarios of sensing a medium, in accordance with embodiments of the invention;

DETAILED DESCRIPTION OF THE INVENTION

Figure 1A:
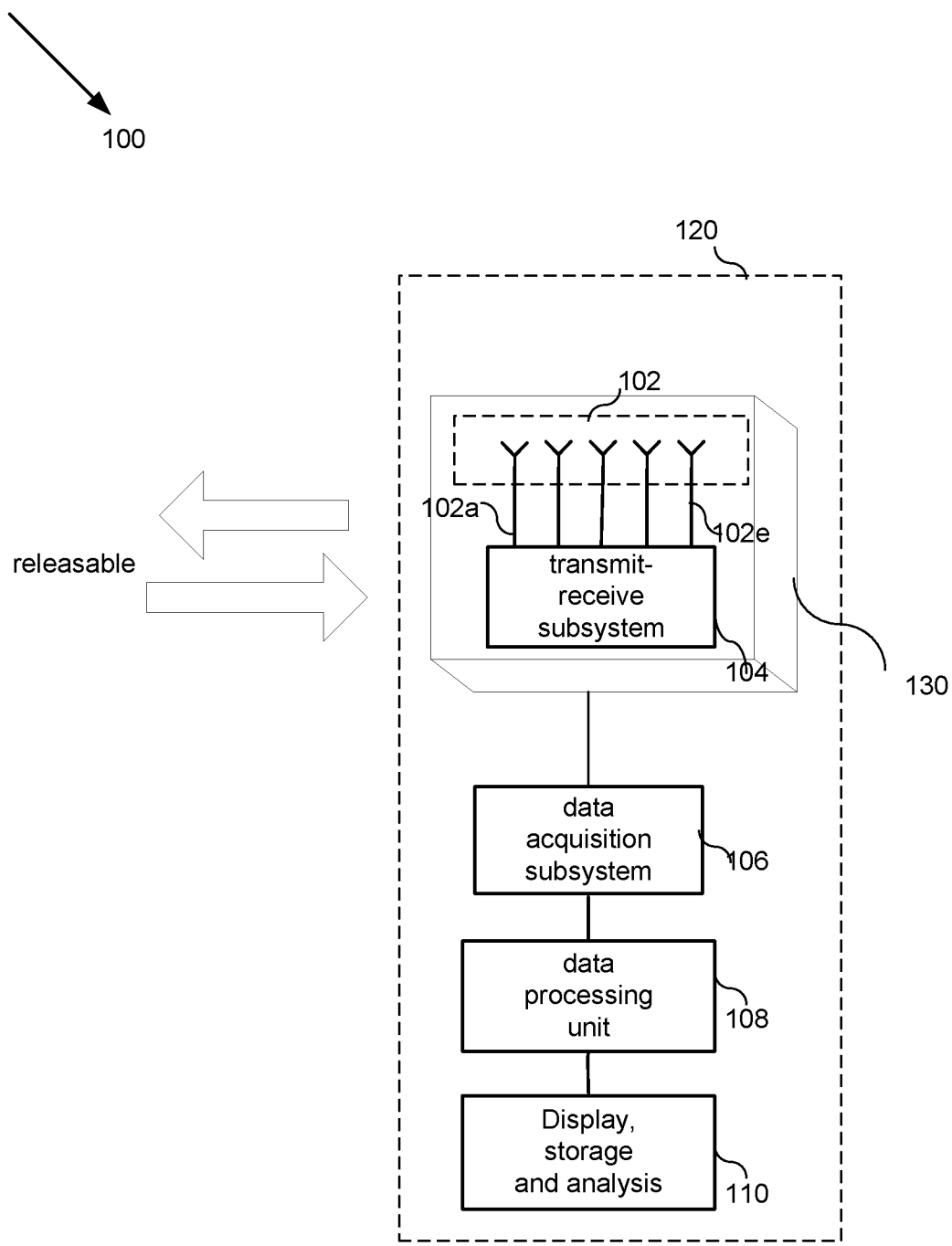
FIG. 1A is a schematic view of a sensing system, in accordance with embodiments of the invention.

The present invention relates to systems devices and methods for measuring the dielectric properties of one or more substances or objects and more specifically, but not exclusively, to sensing substances located in and/or surrounded by a medium such as a non-homogenous medium for example a layered medium, including one or more layers, using Radio Frequency (RF) sensors such as microwave sensors.

The present invention further provides a system and method for analyzing or characterizing an object for example according to impedance measures or dielectric properties of said object or substances using one or more sensors.

According to some embodiments of the invention there are provided methods and systems for estimating media parameters, namely the media's propagation velocity, attenuation and dispersion, for an unknown media (e.g. where the media and/or the objects within the media parameters are unknown) for example, in soil, concrete walls, hollow concrete "blocks", human body (such as breast cancer detection), etc.

According to another embodiment of the invention there is provided a system for sensing at least one substance or a medium comprising an array of sensors. In an embodiment, the array comprises one or more transducers for example at least two transducers, wherein at least one of the transducers is configured to transmit a signal towards the medium or the object, and at least one transceiver attached to the transducers, the transceiver is configured to transmit at least one signal toward the medium and receive a plurality of signals affected by the medium In an embodiment, the array of sensors comprises one or more antennas for example one or more receivers antennas and transmitters antennas or one or more microwave transceivers configured to transmit and receive one or more signals, to sense or image the substance and or medium from one or more locations. Measurements from multiple locations may be obtained by moving the antenna array, for example scanning along the medium surface, or by moving the medium.

It is stressed that the use of the term "sensing" refers to characterization of the media parameters. The term "imaging" refers to identification of structures or targets inside the medium.

In some embodiments the sensing unit (for sensing media parameters) is combined with an imaging unit for imaging the structures within the media. The two units may be combined in several ways. For example, the estimated media parameters may be used as prior information for the imaging algorithm (as will be illustrated herein below). Additionally, the media parameters may be used as additional information on the image (e.g. coloring different materials by different colors). Lastly, according to embodiments of the invention by using auto-focusing algorithms on the image, the estimation of the media parameters may be improved.

In some embodiments, the sensing system may include MIMO (multiple-input and multiple-output) arrays in the microwave region.

The system further includes a transmit/receive subsystem configured to generate and transmit the RF signals. For example these signals may be microwave signals in the UWB band 3-10 Ghz (having a wavelength of 3-10 cm in air), and may be stepped-CW (sinus), chirps, shaped/coded pulses or other waveforms, a Radio Frequency Signals Measurement Unit (RFSMU) such as a Vector Network Analyzer (VNA) for measuring the received/reflected signals, a data acquisition subsystem and one or more processor units for processing the measured signals and characterising the medium.

In operation, one or more signals, such as a predesigned signal are transmitted from one or more of the microwave transceiver antennas of the antenna array and are later received by one or more other antennas. The use of a wide frequency range such as UWB range (3-10 Ghz) allows high temporal resolution. In some cases, the signals utilized for microwave imaging or sensing applications, may be frequency-swept waveforms and/or pulse waveforms.

At the next step the received transmissions are used to estimate a transfer function of the medium located between the transmit antennas and receive antennas. A processing unit processes these signals to generate an estimate of the medium and in addition may generate an image of the medium. In some cases, the image may comprise of an intensity value per, for example 3D voxel, representing the strength of reflection obtained from the respective point in space.

The image reconstruction process includes analyzing a collection of responses yij(t) denoting the impulse response between one or more transducers, e.g., antenna i and antenna j at time t. The responses may be given, for example in frequency domain and converted to time domain by for example Inverse fast Fourier transform (IFFT) algorithm, or by other various algorithms as known to those skilled in the art.

In some cases, the estimation of the transfer functions yij(t) includes a calibration processes as known to those skilled in the art, for example, dividing the frequency domain signal Yij(f) by a reference signal Rij(f) representing for example the responses of the measurement device, traces, antenna elements and so forth.

Examples for embodiments for calibration an antenna array may be found in U.S. patent application Ser. No. 14/499,505, filed on Sep. 30, 2015 entitled "DEVICE AND METHOD FOR CALIBRATING ANTENNA ARRAY SYSTEMS" which application is incorporated by reference herein in its entirety.

An algorithm such as Delay and Sum (DAS) may be used for reconstructing an image from the impulse responses of the medium. Other algorithms may be used for imaging as well. Specifically in DAS, for each point r in some designated volume in the three dimensional space, and for each antenna pair (from antenna i to antenna j) the expected delay from antenna i to point r and back to antenna j is calculated, considering the propagation velocity through the medium (which is assumed to have known electrical properties). Denoting this delay by $T_{ij}(r)$. Then the reconstructed image at location r is created by summing the estimated impulse responses $y_{ij}(t)$ of each pair i,j at the expected delay $T_{ij}(r)$, i.e. according to the following Eq (Equation):

$$I_{DAS}(r)=\Sigma_{ij}y_{ij}(T_{ij}(r))$$

where the summation is over all antenna pairs.

In some embodiments, a function of $I_{DAS}(r)$ such as its absolute or power is presented as the image. Assuming a reflector exists at point r in the medium then a positive pulse is expected to exist at position $T_{ij}(r)$ in all, or most, pairs, creating high intensity of the reconstructed image at this point.

According to some embodiments of the present invention there are provided methods and systems applicable to a number of sensing scenarios as will be further illustrated below.

The methods described herein apply to RF signals. Those skilled in the art would appreciate that the same or similar methods can be adopted for use with other sensing mechanism, for example sonar, ultrasound, optical signals, etc.

The dielectric properties of the medium and/or objects within the medium may be obtained or the medium and/or objects may be imaged according to various methods and systems in accordance with the present invention embodiments described herein.

Estimating Media Parameters from Background Reflections

Disclosed herein are methods and devices for estimating media parameters according to background reflections (e.g. random or irregular reflections) measurements from the medium. In some cases, as will be illustrated in FIGS. 2A and 2B, a scanned medium has inhomogeneity characteristic, this characteristic is utilized according to the present invention for obtaining the medium dielectric properties. For example, in many cases reflections from the medium are generated by irregularities in the medium such as scattering objects (e.g. reflectors) which may be received and measured by a measuring system such as the system of the present invention illustrated in FIG. 1. For example, in sensing a concrete wall, rebars inside the wall or small air cavities may act as the said scaterrers. Other examples are internal organs in a scanned human breast, irregularities in soil (including stones).

In some cases all signal responses from all reflectors are measured and analyzed.

The received reflected or affected signals by the medium are further analyzed by one or more processing units which analyze for example a correlation between the signals, such as all or part of the combined signals reflected from the reflectors, received by different pairs of antennas.

In some cases the processing of the reflected signals includes providing a full covariance matrix of the reflected signals.

In some cases various correlations (e.g. any of a broad class of statistical relationships involving dependence) of one or pairs of antenna are processed, such as correlations of near and/or far pairs of antennas.

In some cases the path loss (a parameter representing the attenuation of the material, excluding space loss, and given, for example, in units of dB/cm) is obtained and processed by the one or more of the processing units, for example by calculating a Power delay profile (PDP).

In some cases the processing of the reflected signals includes obtaining the dielectric properties of the medium $\epsilon_R$ and analyzing the relations between the medium dielectric properties and pathloss to obtain an estimate of the pathloss.

Estimation of Layered Media

In some cases, as illustrated in FIG. 2D, the media may include two or more layers. Particular cases may include for example:

Estimating the media directly interfacing the antenna array (for example, in order to evaluate its effect on the responses of the antenna elements), from the direct signals (as illustrated in FIG. 2C).

Estimating the depth and propagation velocity of a given layer interface by comparison of time delays or by comparison of horizontal and vertical polarized reflection coefficient.

Autofocusing of Targets

In some cases the medium may include one or more targets (e.g. scatterers that can be focused by the imaging algorithm) and the medium's or object's characteristic such as the dielectric properties may be obtained or the medium or object may be imaged by autofocusing of targets and by maximizing the targets strength on the resulting image without reproducing the image.

In some cases the method may include tracking a target through the change of media parameters or by Local ridge alignment.

Medium Estimation Based on Extrinsic Measurements

In some cases the medium's or object's characteristic such as the dielectric properties may be obtained by extrinsically measuring by the antenna array to provide additional or supporting information, or give a starting point for autofocusing. The method based on extrinsic measurements may further include:

Capacitance measurements at varying distances

Combination of information from antennas with other modalities (especially inductive). Prior to the detailed specification of the invention being set forth it may be helpful to set forth definitions of certain terms that will be used hereinafter.

Referring now to the drawings, FIG. 1A illustrates an RF measuring system 100 configured to sense or image a medium and/or objects within the medium, in accordance with embodiments of the invention. The system 100 comprises a measurement unit 130 configured to be attached or included in a device such as a portable device 120. According to some embodiments, the portable device 120 may be a handheld device or a handheld computer such as a mobile telephone, a smart phone, a tablet computing device, a laptop computing device, a personal digital assistant, a visible light camera, a personal video device or a music player, personal media player, global positioning system navigational device, pager, portable gaming device or any other appropriate mobile device known in the art. For example, the measurement unit 130 may be configured to capture, characterize, image, sense, process, and/or identify, or define a medium and/or an object within the medium such as OUT (object under test) and provide an identification results relating to the OUT to the portable device 120 for use in any desired fashion (e.g., for further processing, to store in memory, to display, to use by various applications running on the portable device 120, to export to other devices, or other uses).

In one embodiment, the sensor unit 130 may be a multi-layer structure implemented at least in part with printed circuit board techniques using appropriate dielectric materials. Commonly used materials are glass-epoxy, Teflon-based materials. Layers of high-dielectric-constant materials can be incorporated in order to match the antennas to materials under test.

The measurement unit 130 may include or may be connected to a transmit/receive subsystem 104, a data acquisition subsystem 106, a data processing unit 108 and a console 110.

According to some embodiments of the invention the measurement unit comprises an array, the array comprises one or more transducers, wherein at least one of said at least two transducers is configured to transmit a signal towards a medium or objects, and at least one transceiver attached to the transducers, the at least one transceiver is configured to transmit at least one signal toward the medium and receive a plurality of signals affected by the medium.

Specifically, the measurement unit 130 may include one or more antennas such as antenna array 102. For example the antenna array 102 may include multiple antennas 102a-102e typically between a few and several dozen (for example 30) antennas. The antennas can be of many types known in the art, such as printed antennas, waveguide antennas, dipole antennas or "Vivaldi" broadband antennas. The antenna array can be linear or two-dimensional, flat or conformal to the region of interest.

According to some embodiment of the invention the antenna array 102 may be an array of flat broadband antennae, for example spiral shaped antennae. The antenna array 102 may include a layer of matching material for improved coupling of the antenna radiation to the materials or objects under test. The unique and optimized shape of the antenna array, enables their use in limited sized mobile devices, such as a thin, small-sized smart phone or tablet. In addition, the use of an antenna array made as flat as possible, for example in a printed circuit, allows for the linkage of the measurement unit 130 to any mobile device known in the art, as it does not take up much space in the mobile device, it is not cumbersome, nor does it add significant weight to the portable device 120.

In some cases the measurement unit 130 may be a standalone unit, for example attached to or connected to a computer device via wire or wireless connections such as USB connection or Bluetooth™ or any electronic connection as known in the art.

The transmit/receive subsystem 104 is responsible for generation of the microwave signals, coupling them to the antennas 102a-102e, reception of the microwave signals from the antennas and converting them into a form suitable for acquisition. The signals (e. g. RF signals) can be pulse signals, stepped-frequency signals, chirp signals and the like. The generation circuitry can involve oscillators, synthesizers, mixers, or it can be based on pulse oriented circuits such as logic gates or step-recovery diodes. The conversion process can include down conversion, sampling, and the like. The conversion process typically includes averaging in the form of low-pass filtering, to improve the signal-to-noise ratios and to allow for lower sampling rates. The transmit/receive subsystem 104 can perform transmission and reception with multiple antennas at a time or select one transmit and one receive antenna at a time, according to a tradeoff between complexity and acquisition time.

The data acquisition subsystem 106 collects and digitizes the signals from the transmit/receive subsystem 104 while tagging the signals according to the antenna combination used and the time at which the signals were collected. The data acquisition subsystem will typically include analog-to-digital (A/D) converters and data buffers, but it may include additional functions such as signal averaging, correlation of waveforms with templates or converting signals between frequency and time domain.

The data acquisition subsystem 106 may include a Radio Frequency Signals Measurement Unit (RFSMU) such as a Vector Network Analyzer (VNA) for measuring the received/reflected signals.

The data processing unit 108 is responsible for converting the collected signals into a set of responses characterizing the OUT, and performing the algorithms for converting the sets of responses, for example into medium sensing data.

An example of algorithm for converting the sets of responses may be for example Delay and Sum (DAS) algorithm described above.

Typical image reconstruction algorithms (such as DAS) assume perfect antenna elements, and therefore the above effects are compensated before applying the reconstruction algorithm, e.g. by dividing the frequency response obtained from the measurement by the known frequency response of the components.

Examples for such algorithms may be found in US Patent Application Publication No. US20140066757, entitled "WIDEBAND RADAR WITH HETEROGENEOUS ANTENNA ARRAYS" which application is incorporated by reference herein in its entirety.

A final step in the process is making use of the resulting parameters or image, either in the form of visualization, display, storage, archiving, or input to feature detection algorithms. This step is exemplified in FIG. 1A as console 110. The console for example in a mobile device is typically implemented as a handheld computer such as a mobile telephone or a table computer with appropriate application software.

According to system type, the computer can be stationary, laptop, tablet, palm or industrial ruggedized. It should be understood that while FIG. 1A illustrates functional decomposition into processing stages, some of those can be implemented on the same hardware (such as a common processing unit) or distributed over multiple (such as graphical processing unit, GPU) and even remote pieces of hardware (such as in the case of multiprocessing or cloud computing).

According to one embodiment of the invention, subsystems 106, 108 and 110 may be part of the measurement unit or the portable device 120, as shown in FIG. 1A. Alternatively the measurement unit 130 may be included within a housing 125 such as case or a jacket configured to be releasable (i.e. connected or disconnected) to the portable device 120. For example the measurement unit 130 may include the antenna array unit 102 and the transmit/receive-subsystem 130 may be part of the housing 125 which is electrically or wirelessly connected to the portable device 120, for example through a dedicated connection such a USB connection, wireless connection or any connection known in the art.

Following the connection of the sensor unit 130 to the portable device, the sensor unit 130 may utilize the portable device's own data acquisition, data processing display, storage and analysis subsystems.

Figure 1B:
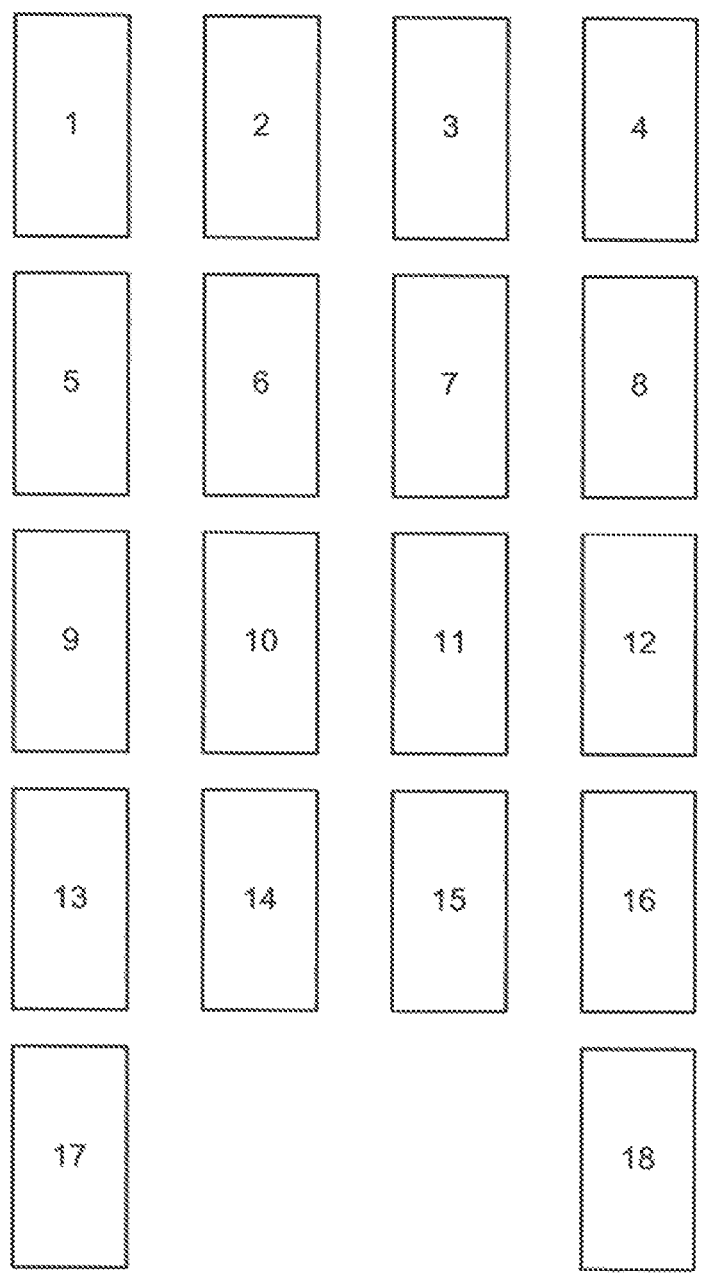
FIG. 1B is a schematic view of an antenna array, in accordance with embodiments of the invention.

FIG. 1B schematically illustrates an antenna array according to an embodiment of the present invention, the planar antenna array comprises of 18 antennas arranged with equal distances of for example about 2 cm (in some embodiments the distance may be smaller or larger) and configured for transmission and reception in the UWB frequency range.

FIGS. 2A and 2B schematically illustrate a medium 220 including a plurality of scattering reflectors and the distribution of scattering radio signals reflected through the medium 220. FIG. 2A shows an antenna array 210 such as linear antenna array placed in front of a dielectric medium 220 wherein the medium comprises a plurality of scattering objects such as objects 221. The antenna array 220 is configured to transmit and receive radio signals reflected or affected from or by the objects 221 and the processing unit as shown in FIG. 1 may process the reflected or affected signals for obtaining the dielectric properties of the medium and/or the objects and possibly further providing an accurate image of the medium content.

The antenna array may comprise 2, 3 4, 5, 6, 7, 8, 9, 10 or more antennas positioned for example respectively vertically along a Y axis of a Cartesian coordinate system. As shown in FIG. 2A the antenna array 210 may include six antenna 211, 212, 213, 214, 215 and 216 positioned few cm from one another for example about 2 cm in proximity or attached to the medium 220. In some embodiments, each antenna may be a transmitter or receiver or a transceiver antenna. In some embodiments, several antennas of the antenna array may be transmitting antennas and some receiving antennas. The antennas may be of any type of antennas known in the art.

The medium 220 comprises a number of scattering objects (e.g. reflectors) of various size such as reflectors 221, 222, 223 and 224.

FIG. 2B is a schematic illustration of some of the reflections from the reflectors inside the media. For example radio signals 231 and 232 transmitted by antenna 211 may be reflected, affected or scattered by reflectors 223 and 224, accordingly and received as signals 231' and 232' at antenna 212.

According to one embodiment of the invention the media dielectric parameters may be obtained by measuring a plurality of direct links between pairs of antennas as will be illustrated below in respect to FIG. 2C.

FIG. 2C shows the direct links (TX to RX) between antennas (e.g. two links are drawn for illustration, out of the $$\frac{N(N-1)}{2}$$

possible links assuming each antenna may be used as transmitter or receiver). For example measuring respectively the direct links 251 and 252 between antenna elements 211 and 216 and antenna elements 212 and 214.

FIG. 2D illustrates a layered media 270, comprising for example two layers a first layer 272 and a second layer 274. The width of each layer may be anything between a fraction (for example 0.25 or smaller) of a wavelength to many (for example 100) wavelengths. The layers type may be for example a layer of stucco on top of a concrete wall, or layers in a human body, in soil, or a body of fluid with air above it. In some cases the direction of the interface between the layers may be known, and in some cases parallel to the array (for example layers in cement blocks), and only the depth and the dielectric properties are unknown. There may be several such interfaces, for example a hollow block comprised of a layer of concrete and cavity of air, and coated with stucco (three layers). Reflectors which are of interest for imaging may exist at both sides of the interface.

Estimating Media Parameters from Background Reflections

According to some embodiment of the present invention there are provided methods and systems for estimating media parameters, for example to image the media and objects within the media, according to the media background reflections. The methods and systems of the present invention assume the medium includes multiple small scattering objects (e.g. reflectors). This assumption is correct in many cases, as any local non-homogeneity such as cracks in concrete, air cavities in blocks, or blood vessels in fatty tissue may produce a small reflection. According to these methods the responses such as the overall responses from all reflectors are used, without focusing on any specific reflector, to obtain information on the medium and more specifically to image the medium.

According to one embodiment of the invention there is provided a method for sensing a medium, wherein the medium parameters are unknown, comprising obtaining by a system such as the RF and data acquisition system of FIG. 1A a number of signals reflected or affected from or by the reflectors in the medium and processing the correlation between the signals obtained by different antennas, such as antenna pairs of an antenna array and combining the correlations to yield an estimate of the media parameters.

For example as shown in FIG. 2B the antenna array 210 such as linear antenna array placed in front of a dielectric medium 220 wherein the medium comprises a plurality of scattering objects such as objects 221,222, 223, 224 and 225. The antenna array 220 is configured to transmit and receive radio signals reflected from the objects the processing unit as shown in FIG. 1A may process the reflected (affected) signals, according to FIG. 3.

Figure 3:
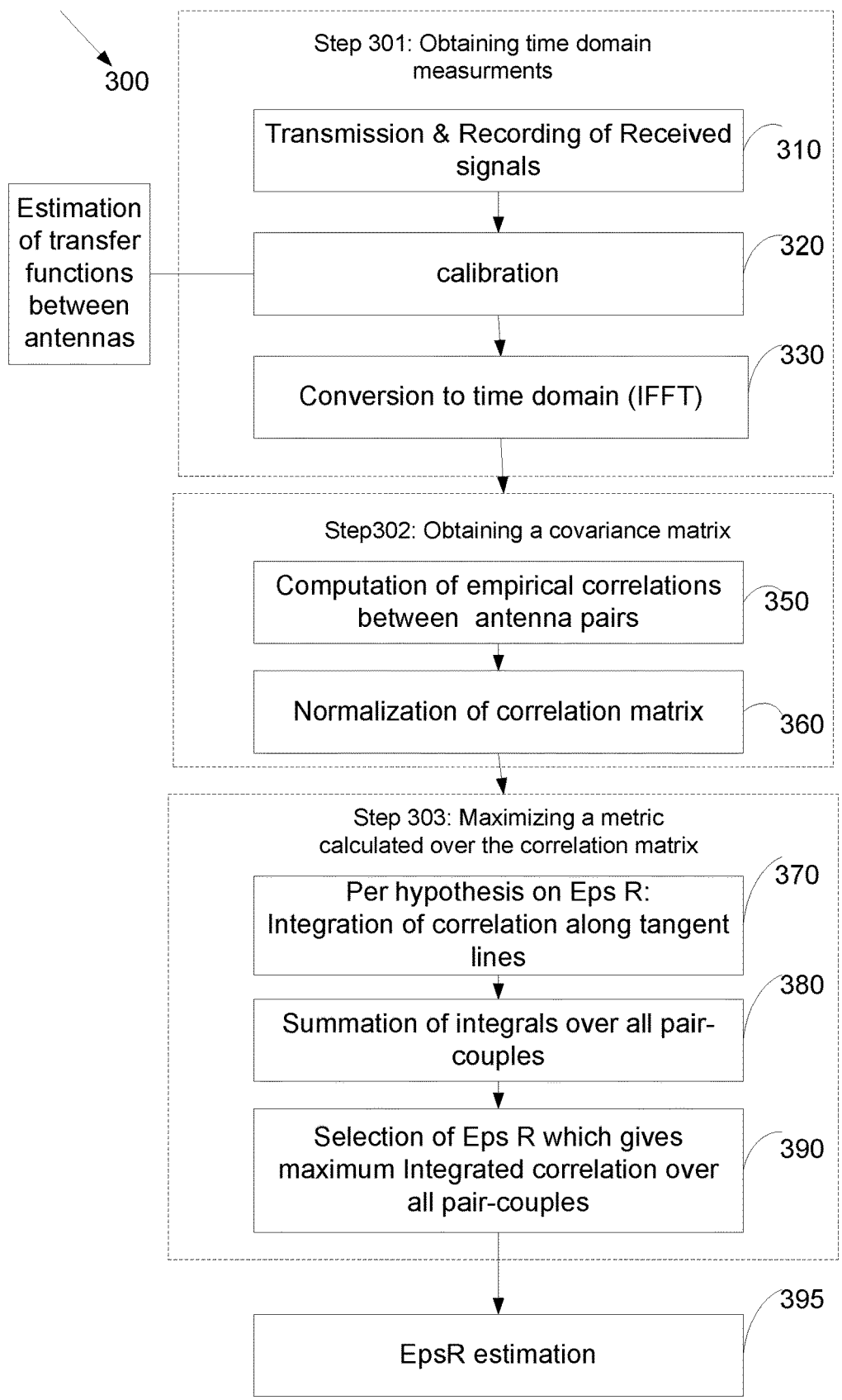
FIG. 3 is a flowchart of a method for estimating media parameters, such as the dielectric constant EpsR, based on to a plurality of background reflector affected by the media, in accordance with embodiments of the invention.

FIG. 3 is a flowchart of a method 300 for estimating media parameters, such as the dielectric constant EpsR, based on to a plurality of background reflector (e.g. random or irregular reflections), reflected from the media. The method includes three main steps:

Step 301: Obtaining time domain measurements. This stage includes the following steps. At step 310 a plurality of signals are transmitted by an antenna array, such as the antenna array of FIG. 1A. The reflected or affected signals reflected or affected from or by the scattering objects within the media are received by the antenna array and are recorded for example by the processor of system 100. At step 320 the system is calibrated. The calibration is performed by the processing unit and includes dividing the signals by reference signals representing the responses of the measurement device, traces, antenna elements and so forth. Following the calibration process the transfer functions between the antennas of the antenna array are estimated at step 330. At step 340 the estimated transfer functions are converted to time domain for example by an IFFT methods. Other methods as known in the art may be used to convert the functions.

Step 302: Obtaining a covariance matrix. This step includes the following steps. At step 350 an empirical correlations between the antenna pairs are computed and obtained to yield a correlation matrix of the signal correlations of the antenna pairs. At step 360 the correlation matrix is normalized. The normalization includes division of each covariance term between two signals by the product of the standard deviations of the signals (to obtain a correlation factor). In some cases (for example when estimating path loss) the normalization may be avoided.

Step 303: Estimating the parameters by maximizing a metric calculated over the correlation matrix. This step may be performed in different ways for estimation of different parameters. The flow described in FIG. 3 is specific for estimation of EpsR and is described in more detail below. Other ways for estimation of media parameters are described further herein. For estimation the EpsR, step 370 includes a hypothesis process to obtain the medium's Eps R. The hypothesis includes integration of correlation along tangent lines of antenna pairs of the antenna array to yield a plurality of integrals of pair of antennas. The tangent line is defined herein below in respect to FIG. 7. At step 380 the plurality of integrals for example over all antenna pairs are summed and at step 390 the Eps R which results in a maximum integrated correlation over all pairs of antennas is selected as the medium's Eps R (step 395).

Steps 360-395 are herein described in detail. Consider for each point p in space and each antenna pair, the ellipsoid of all points p' having the same distance from the pair (i.e. from the TX antenna to p' and back to the RX antenna) asp. If for two pairs there is a line in space on which the aforementioned ellipses of the two pairs are tangential then this line is termed the "tangent line". Reflectors along this line create strong correlations over the time domain signals.

Figure 7:
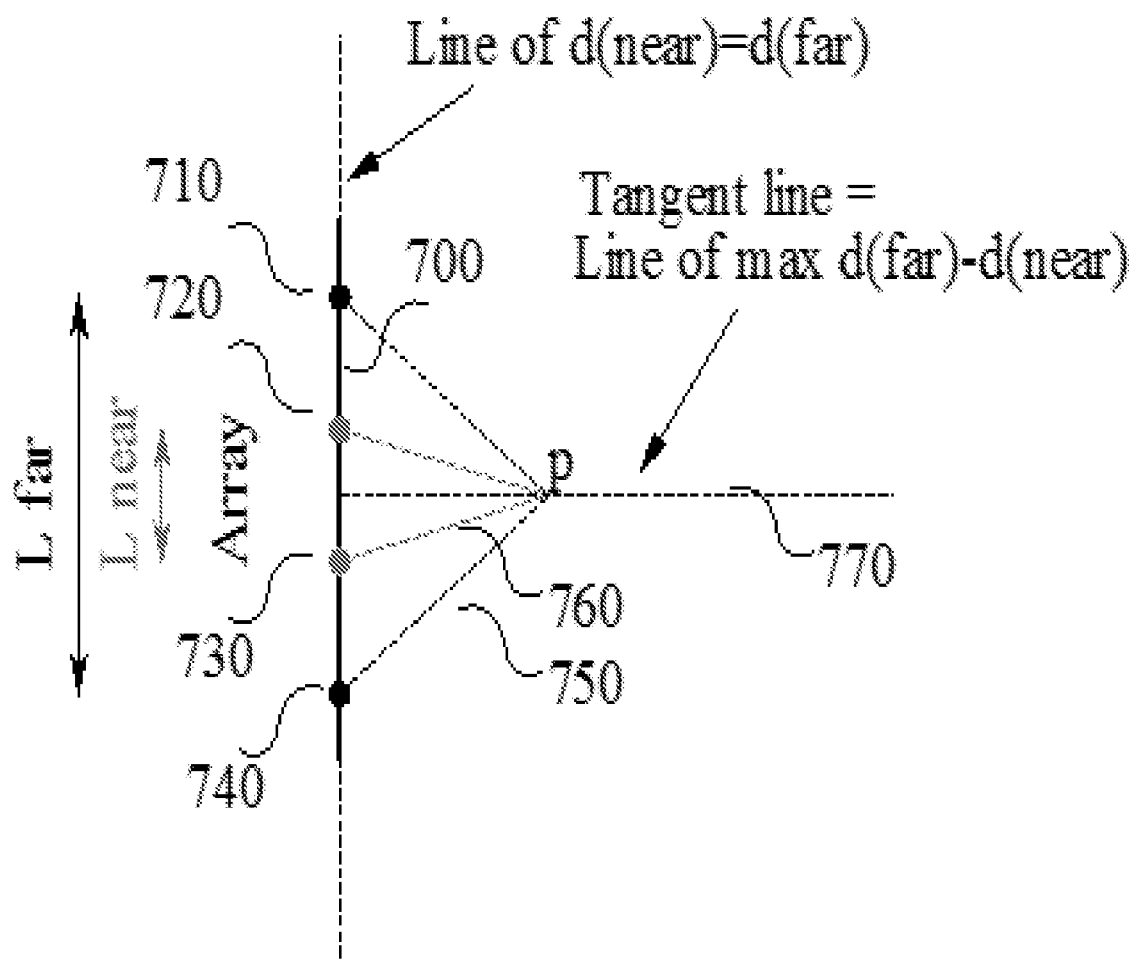
FIG. 7 illustrates a linear array and the relation of distances between near and far pairs, in accordance with embodiments of the invention.

For antenna pairs having the same, or a similar, geometric centers (e.g. the center of the line between the antennas) there is a significant correlation between different time instances, because their same-delay ellipsoids overlap for a wide area around a line passing through the center of the antenna pairs. In this case the tangent line is the line passing through the center (see FIG. 7). For example a reflector appearing at time $t_1$ in one pair, would typically appear at or around time $t_2$ in the other pair, where the relation between the times is related to the propagation velocity. For example, as illustrated in FIG. 7A linear antenna array 700 comprises two pairs of antennas 710,740 and 720,730, where antennas 720,730 are termed 'near' pair antennas and antennas 710, 740 are termed as 'far' pair. Antennas 710 and 720 may be transmit antennas and antennas 730 and 740 may be receive antennas or vice versa. For any given point p in space, $d_{far}$ (750) and $d_{near}$ (760) denote the travel distances of the respective pair associated with that point (from the transmit antenna, to the point in space and then to the receive antenna). It is easy to see that $d_{far} \geq d_{near}$, and their maximum difference for a point at depth z is $$d_{far} - d_{near} = 2\sqrt{z^2 + \left(\frac{L_{far}}{2}\right)^2} - 2\sqrt{z^2 + \left(\frac{L_{near}}{2}\right)^2}$$

and diminishes with depth. This relation between $d_{far}$, $d_{near}$ generates a relation between the propagation times $t_{far}$, $t_{near}$ from which the propagation velocity can be estimated. In this case, the tangent line (770) is also the line of maximum difference.

A method for estimation of EpsR, in accordance with embodiments of the invention includes the following steps:
  1. For each couple of antenna pairs ((tx1,rx1),(tx2,rx2)), calculate the tangent line (if exists). In the following calculations, include only pair-couples having a valid tangent line(s).
  2. Convert the signals after calibration of the responses of the measurement system, the traces/cables and the Tx/Rx antennas (step 320) into time domain (step 340). If the antenna responses depend on the interfacing material then the latter can be estimated using the methods described below for estimating the interfacing media.
  3. Calculate a covariance matrix for each pair-couple (where both axes of the matrix are in time units). Average this covariance over all locations and all pair-couples with the same configuration (step 350), i.e. having the same distance between antennas for each of the antenna pairs involved.

$$\Lambda_{ij}(t_1,t_2) = \hat{E}[y_i^{(k)}(t_1) \cdot y_j^{*(k)}(t_2)] - \hat{E}[y_i^{(k)}(t_1)]\hat{E}[y_j^{*(k)}(t_2)]$$

where $y_i^{(k)}(t)$ is the time domain signal obtained at instance/location k belonging to pair i at time delay t, and $\hat{E}[\ ]$ denotes empirical mean $$\left(\text{e.g. } \hat{E}[A_k] \stackrel{def}{=} \frac{1}{K}\sum_{k=1}^{K} A_k\right).$$

Alternatively, the matrix $\Lambda_{ij}$ can be obtained by representing each measurement $y_i^{(k)}(t)$ as a vector of samples for different values of t, and $\Lambda_{ij}$ is the covariance matrix between the vectors representing $y_i^{(k)}$ and $y^*{}_j^{(k)}$ over all k.

Figure 8:
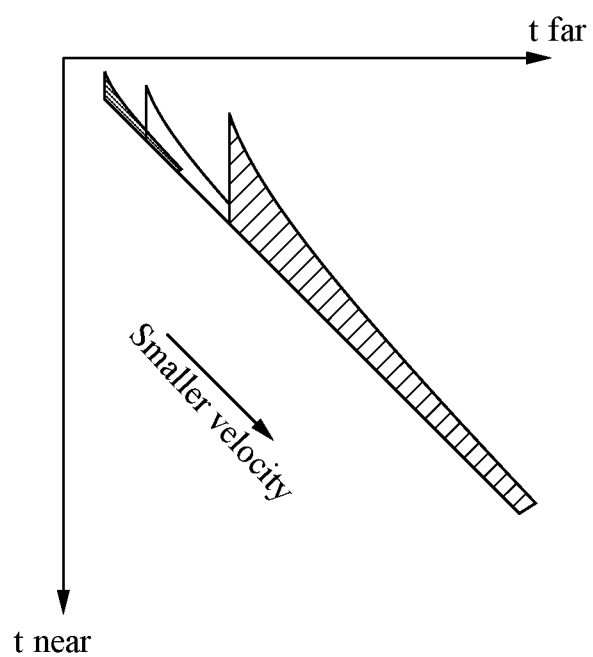
FIG. 8 illustrates a simulation graph of a relation between time of arrival at near and far pair of antennas, in accordance with embodiments of the invention.

4. Normalize the covariance matrix by the standard deviation of each pair separately to convert it to correlation factor $$\rho_{ij}(t_1, t_2) = \frac{\Lambda_{ij}(t_1, t_2)}{\sqrt{\Lambda_{ii}(t_1, t_1)\Lambda_{jj}(t_2, t_2)}},$$

where $\Lambda_{ij}(t_1, t_2)$ denotes the covariance between the signals of pair i at time $t_1$ and pair j at time $t_2$ (step 360). Such an exemplary time-domain covariance matrix extracted for two pairs is shown in FIG. 8. The dominant "ridge" seen in the covariance matrix corresponds for the delays characterizing the tangent line of the said pairs.

5. Integrate the normalized covariance $\rho_{ij}(t_1, t_2)$ along the tangent line of pairs i,j (step 370). More explicitly, this tangent line passes through points [x(h),y(h),z(h)] in space (where h is a parameter), and generates distance $d_i(h)$ from pair i and $d_j(h)$ from pair j, then under the hypothesis of propagation velocity v, we calculate $$S_{ij}(v) = \int \rho_{ij}\left(\frac{d_i(h)}{v}, \frac{d_j(h)}{v}\right).$$

dh. In some embodiments of the invention, this integral is calculated separately for different range gates, in order to estimate the velocity at each range separately.

6. Sum the integrals obtained for each pair-couple to obtain the maximization metric $\mu(v)=\Sigma_{ij}S_{ij}(v)$ (step 350) and find the propagation velocity $$v = \frac{c}{\sqrt{\epsilon_R}}$$

that maximizes the result (step 390).

Estimation by Comparison to a Covariance Matrix

According to another embodiment of the present invention the medium may be estimated by comparison of the medium obtained signals to a covariance matrix. This way generalizes the algorithm described above and enables estimating other medium parameters in addition to EpsR. The method comprising providing a model, the model configured to generate (e.g. either explicitly or implicitly) a computed covariance matrix for every value of the medium's parameters. This covariance matrix is compared against an empirical covariance of the measured signals (obtained in step 302) defined below using a comparison metric. The value of the parameters that maximizes the comparison metric is chosen as the estimate of the medium parameters. These steps may replace steps 370, 380 in step 303 of flowchart 300.

Let y denote a vector of measurements from all available antenna pairs in all frequency or time samples. The measurement may be performed in frequency or time domain but regardless, it may be converted to frequency or time domain as convenient for the purpose of estimation. In the vector y all measurements are concatenated in some prescribed order (for example, pair-first then frequency). Let θ denote the unknown medium parameters (e.g. possibly a vector).

The estimation method by comparison to a covariance matrix includes the following steps: (a) obtaining a computed covariance matrix $\Lambda_\theta$ for every value of the unknown parameter, (b) obtaining an empirical covariance matrix $\Lambda_y$ from the measured signals and (c) calculating a comparison metric μ which is a function of $\Lambda_\theta,\Lambda_y$ and finding the value of the parameters θ that maximizes this metric.

Step (a): Let $Y_\theta$ be a theoretical random variable with the same structure of y, for a given value of the parameters. The computed covariance matrix is $\Lambda_\theta=E[Y_\theta Y^*{}_\theta]$ where [ ]* denotes Hermitian conjugate. For example, if the reflection of a unit-reflector at point r in space is modelled as a vector h(r;θ) (with the same structure as y), and the reflectivity of targets is assumed to be zero-mean and independent between locations, then $\Lambda_\theta$ may be computed as $\Lambda_\theta=c\cdot\int_{r\in R^3}h(r;\theta)h^*(r;\theta)f(r)dr$ where f(r) is the assumed power-density associated with the reflectors (as an example, a uniform distribution in space). The integral does not explode due to space loss component in the model h(r;θ). The covariance matrix is usually known only up to a constant, because the actual number and intensity of reflectors is not known.

In step (b) we compute $\Lambda_y$, the empirical covariance of y. For the case of multiple measurements (for example, a result of a scan of the medium), $$\Lambda_y = \frac{1}{N}\sum_n y_n y_n^*.$$

For the case of a single measurement $\Lambda_y=y\cdot y^*$. The latter case is not degenerate as it would initially seem, because even a "single" measurement includes multiple values which are averaged-out by the comparison metric. For example, in the case of the aforementioned scan, it is also possible to concatenate all N measurement-vectors into a single vector, and apply the relevant channel model.

The comparison metric computed in step (c) compares $\Lambda_y$ and $\Lambda_\theta$. Several possible metrics are given below:

$$\mu_1(y;\theta)=c_1(\theta)\cdot tr(\Lambda_\theta\Lambda_y)=c_1(\theta)\cdot y^*\Lambda_\theta y$$

$$\mu_2(y;\theta)=-c_2(\theta)\cdot tr(\Lambda_\theta^{-1}\Lambda_y)=-c_2(\theta)\cdot y^*\Lambda_\theta^{-1}y$$

$$\mu_3(y;\theta)=-c_3(\theta)\cdot tr((\Lambda_\theta+\lambda I)^{-1}\Lambda_y)=-c_3(\theta)\cdot y^*(\Lambda_\theta+\lambda I)^{-1}y$$

The expressions on the right hand side show the value of these metrics for the single measurement-vector case. The normalization functions c(θ) ($c_1(\theta)$, $c_2(\theta),c_3(\theta)$) are independent of the measurements y and their role is to prevent a bias of the estimator. The metric $\mu_1$ in general emphasizes the similar parts between $\Lambda_\theta,\Lambda_y$ (i.e. gives a positive weight for properties of y that exist in $\Lambda_\theta$), while the metric $\mu_2$ penalizes the non-similar parts (i.e. gives a negative weight for properties of y that do not exist in $\Lambda_\theta$). As a result $\mu_2$ produces a sharper estimate but is more sensitive to model assumptions. $\mu_3$ enables to trade-off these two properties using the parameter $\lambda$ (behaves like $\mu_2$ for small $\lambda$ for like $\mu_1$ for large $\lambda$).

Clearly other metrics for comparison between matrices can be used as well.

Finally, the estimated value of the medium parameters is:

$\hat{\theta}=\text{argmax}\{\mu(y;\theta)\}$

It is stressed that while this method is used for estimation of media parameters, it may be applied for other unknown parameters associated with the reflection model, including media and target parameters. For example, the dominant polarization, frequency response, or any other average parameter of the targets may be estimated.

As an example, consider scanning of the unknown media using only a single pair of antennas. N Measurements are taken at known locations. Let us suppose the received signals are given as discrete-time signals $y_n(t)$. In that case the vector y includes the values of $y_n(t)$ for all n, t. The computed covariance matrix $\Lambda_\theta$ accounts for correlations between different time instances in different measurement locations (as example the correlation between $y_n(t_1)$ and $y_{n+\Delta}(t_2)$ over all values of n).

It is further stressed that while the dimension of the covariance matrix $\Lambda_\theta$ may be very large, it does not have to be computed, nor its inverse has to be found, in order to evaluate these metrics. Numerical manipulations can be applied in order to avoid these computations. As an example, given the integral form $\Lambda_\theta = \int_{r \in R^3} h(r;\theta) h^*(r;\theta) f(r) dr$, multiplying vector by this matrix (computing $\Lambda_\theta x$) is accomplished by computing $\int_{r \in R^3} h(r;\theta)(h^*(r;\theta)\cdot x) f(r) dr$ where $h^*(r;\theta)\cdot x$ is a scalar, so the matrix is never computed. Computing $\Lambda_\theta^{-1} z$ for a vector z involves solving the linear equation $z = \Lambda_\theta x$, which can be done iteratively, for example using a fixed-point method (see "Numerical Methods Solving Linear Systems Sparse Matrices, Iterative Methods and Non-Square Systems" by Aleksandar Donev).

The methods described above include a calculation of a covariance matrix, however all calculations can be equivalently implemented without explicitly calculating the covariance matrix, as demonstrated by the equations of $\mu_*(y;\theta)$ in clause herein above, which show that the same values can be written as function of the empirical covariance matrix or of the measured signals.

Estimating Path Loss by Power-Delay-Profile (PDP)

According to some embodiments of the invention the medium's path loss, e.g. the average path loss (dB per centimeter or meter) may be obtained using correlations. PDP is the average energy in a certain time-delay. It can be averaged over some or all antenna pairs and all locations. In the simple case, assuming the delay is proportional to depth (denoted z), and the number of targets at range r behaves like $O(r^2)$, the following computation shows that $$PDP(t) \propto \frac{1}{t^2} \cdot 10^{-\frac{PL_{dBcm}}{10} 100 \cdot tv}$$

Where v is the propagation velocity.

If the propagation velocity is known, it is easy to extract the path-loss in dB/cm, $PL_{dBcm}$, after fitting the empirically measured PDP with the equation above. As an example, the decay rate of $PDP(t) \cdot t^2$ computed in decibels/sec can be estimated from the measured PDP, and then divided by $100 \cdot v$ to yield $PL_{dBcm}$. Alternative path-loss or reflector distribution models can be easily accommodated.

Utilizing Relations Between $\epsilon_R$ and Pathloss

In some embodiments of the invention, a relation exists between the dielectric constant $\epsilon_R$ and the pathloss of the medium. For example, both pathloss and $\epsilon_R$ may be a function of the percentage of water in a given basis material. In this case the methods described above may be adapted to take advantage of this relation. In the method of comparing to a simulated covariance matrix, the parameter vector $\theta$ is reduced from two parameters (velocity and path-loss) to one, thus reducing complexity and improving accuracy. In the method of using correlations of near and far pairs, the estimate of propagation velocity using this method can be used to produce an estimate of path-loss through the known relation between them.

Estimation of Directly Interfacing Media

According to another embodiment of the invention, there is provided a method for estimation of directly interfacing media. According to this method, the propagation velocity and path loss of the media directly interfacing the antenna array is estimated from the signals (for example as shown in FIG. 2C). The direct signal between the TX and RX antennas propagates as a lateral (surface) wave along the interface, and is evanescent in the direction pointing toward the medium.

In some cases, the array such as antenna array 210 may be shielded from the back side of the antennas by metal layers, RF cage, or absorbing materials, in order to minimize interference. Thus, the wave is guided to propagate through the interfacing media 220. The method for estimation of directly interfacing media mainly measures the medium at the vicinity of the array, for example 1 mm or less or more than 1 mm for example between 1-100 mm. The direct signal (sometimes termed direct "leakage") is in many cases the strongest signal received.

A challenge of using the direct signal is that it is transmitted through a sidelobe of the antenna element (perpendicular to the direction of main radiation), which is not designed to be efficient or repeatable. Therefore the estimation procedure does not assume the transfer function of the antenna element in the direction of the lateral wave is known. This unknown transfer function is resolved by using relations between different pairs of antennas, and measuring relative delay (and possibly path loss).

It is assumed that for two antenna pairs in which the antenna elements have the same polarization relative to the direction of the path between the antenna, the antenna responses are the same, e.g. for two such pairs (denoted "sig" and "ref"), the responses in frequency domain can be described according to the following Eq:

$H_{sig}(f) = T(f) \cdot P_{sig}(f) \cdot R(f)$ $H_{ref}(f) = T(f) \cdot P_{ref}(f) \cdot R(f)$ Where T(f), R(f) are frequency responses of the transmit and receive elements, which are assumed to be equal between the paths, and $P_{sig}(f)$, $P_{ref}(f)$ are the paths. The method includes measuring the difference between the paths $P_{sig}(f)$, $P_{ref}(f)$, either in arrival time or in power.

In some cases, the following two algorithms may be used to estimate the interface (dielectric material) parameters.

Algorithm (a): Cross Correlation (or Interferometric) Algorithm:
1) Average all signals for a given pair over the sweep and:
   a) By default, use this average for the next stages;
   b) In some applications, use the signals per-scan for the next stages
   c) In some applications for non-homogenous material, subtract the average and then continue. The implication is that the parameters are estimated not based on the average response, but rather based on the average correlation, where correlation is taken over different perturbations in the material.
   d) In some applications, average all pairs having the same antenna configuration and distance before continuing (i.e. before cross-correlation).
2) Time-window the signals of each antenna pair to the delay range $[0, T_{pair}]$ where $$T_{pair} = T_{const} + \frac{D_{pair}}{c}\sqrt{\epsilon_{R,max}}.$$

Time windowing of a signal X(f) with time domain representation (inverse Fourier transform) x(t) means applying a window to x(t), i.e. x'(t)=x(t)·w(t), where w(t) is zero outside the range t∈[0, $T_{pair}$] and may be for example 1 inside the window, or equivalently in frequency domain, applying a respective filter X'(f)=X(f)*W(f), where W(f) is the Fourier transform of w(t).
3) Potentially compensate the signals for pathloss and/or space-loss by multiplying by a gain which is a function of $D_{pair}$ (the antenna-to-antenna distance of each antenna pair).
4) Choose signals from specific pair-couples, for which the relation between the paths is known (i.e. antenna polarization relative to the path direction is the same), and the path lengths in the media differ. As an example, in the 2D array of FIG. 1B, the pair (1-2) can be used as reference for the pair (1-3), and the pair (1-6) can be used as reference for the pair (1-16). The path length in the media is defined as the part of the shortest-time path between the TX and RX antennas, which is travelled within the media. In the case of homogenous media attached to the antenna array, the path length within the media is simply the distance between antennas. Referring for example to FIG. 2c, the path length of the pair 211 to 216 is the distance 251 between the antennas.
5) Specifically in a linear two-dimensional array step (4) may be implemented by:
   a) For each column and each polarization, choose the antennas of that column in the given polarization, and sort them according to their location along the Y axis.
   b) Choose quadruples of antennas satisfying: $i_1 \le i_2 < i_3 \le i_4$.
   c) The signal pair is $i_1, i_4$ and the reference pair is $i_2, i_3$.
   d) Repeat this for all combinations. Notice that the same signal pair may appear several times with different reference pairs, and vice versa.
   e) Repeat the process inverting rows and columns.
6) Conjugate-Multiply the signals of the main channel with the reference channel, for each signal-ref couple:

$$H_{cal}(f) = H_{sig}(f) \cdot H^*_{ref}(f)$$

7) Convert the signals from frequency domain to time domain (using real-valued transform to obtain the real-valued reflection, i.e. x(t)=Re[FFT(X(f))]). Potentially a frequency-window can be applied at this stage. Alternatively, if the signals are given at time domain, $h_{cal}(t)$ is obtained by cross-correlating $h_{sig}(t)$ with $h_{ref}(t)$.
8) Convert the time domain signals $h_{cal}(t)$ to $\epsilon_R$ domain by setting $$t = \frac{D_{sig} - D_{ref}}{c} \cdot \sqrt{\epsilon_R}$$

$$x_{(sig,ref)}(\epsilon_R) = h_{cal}(t)$$

9) Sum the signals for all pair-couples:

$$X(\epsilon_R) = \sum_{\{sig,ref\}} x_{(sig,ref)}(\epsilon_R) = \sum_{\{sig,ref\}} h_{cal}^{(sig,ref)}\left(t = \frac{D_{sig} - D_{ref}}{c} \cdot \sqrt{\epsilon_R}\right)$$

10) Choose the (positive) maximum of $X(\epsilon_R)$ as an estimate for $\epsilon_R$.
11) In some applications it is desired to ignore the amplitudes. In this case it is possible to normalize $x_{(sig,ref)}(\epsilon_R)$ by their maximas before summation, or to use instead of $X(\epsilon_R)$ the relative number of signals $x_{(sig,ref)}(\epsilon_R)$ which have a positive peak at $\epsilon_R$.

To estimate path loss, instead of cross-correlating the signals, the ratio of powers (averaged over frequency domain, in the time window) is calculated. This ratio is compared with the expected space loss of the surface wave, and from this relation the pathloss is estimated.

The measured media interfacing the system may be for example less than 1 mm or 1, 2, 3, 4, 5, 6, 7, 8, 9, 10 mm or more from the sensing system. In some cases the system may be attached to the media surface as illustrated in FIG. 2, or may be placed in proximity to the media's surface, few mm or cm from the media. As shown in FIG. 2C the parameters of the media are obtain according to an analysis of a plurality of RF links between the antennas of the antenna array as shown in FIG. 7

Figure 4:
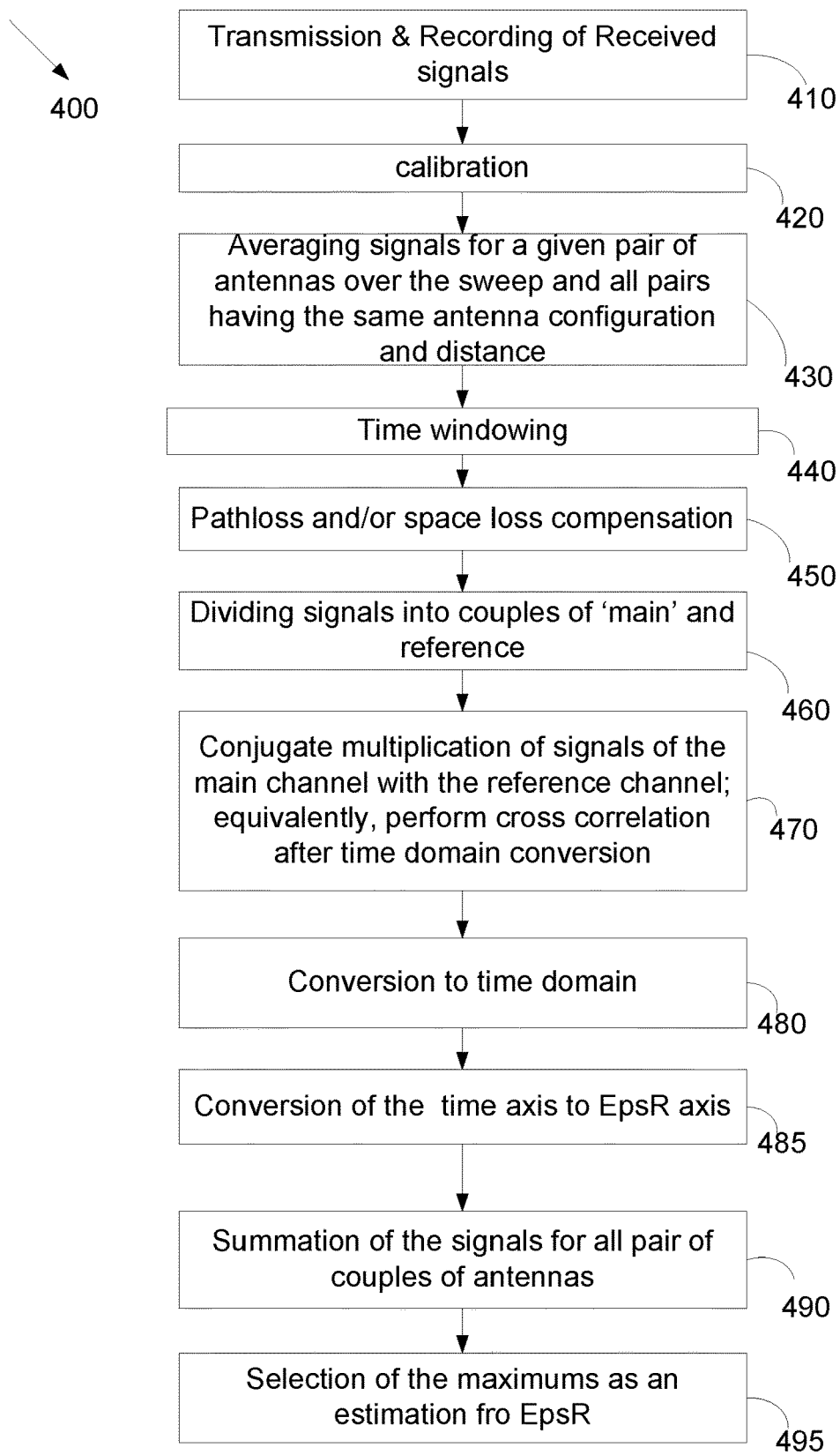
FIG. 4 is a flowchart of a method for estimating parameters, such as EpsR of the media directly interfacing the sensing system, in accordance with embodiments of the invention.

FIG. 4 is a flowchart 400 of a method for estimating parameters, such as EpsR of the media directly interfacing the sensing system. At step 410 a plurality of signals are transmitted by an antenna array, such as the antenna array of FIG. 1A. The reflected (or affected) signals reflected from the scattering objects within the media are received by the antenna array and are recorded for example by the processor of system 100. At step 420 the system is calibrated. The calibration is performed by the processing unit and includes dividing the signals by reference signals representing the responses of the measurement device, traces, antenna elements and so forth. Following the calibration process the received signals for a given pair of antennas over the sweep and all pairs of antennas having the same antenna configuration and distance are averaged at step 430. At step 440 time windowing may be applied to the averaged signals and in step 450 a pathloss and/or SPA compensation process is performed. At step 460 the signals are divided for example to two groups of coupled signals defined as 'main' signals and 'reference' signals (as defined in detail above). At step 470 the 'main' channel signals are multiplied by the conjugate of the 'reference' signals. As an alternative but equivalent implementation, following the time domain conversion of the signals a cross correlation processing of the signals may be performed. At step 480 the signals are converted to time domain and at step 485 the time domain signals are converted to yield a EpsR of the media according to the formula described in step (8) of the present invention. At step 490 the processed signals of all pair couples of antenna are summed and at step 495 the EpsR which provides maximum sum is selected.

Algorithm (b) for Estimation of Directly Interfacing Media: Best-Fit Algorithm

Denote by Y(f,d,c) the signal at frequency f and antenna distance d in pairs with configuration c, where "configuration" shall be defined in the following. The following model is assumed:

$$Y(f,d,c) = A_c(f) \cdot P_\theta(f,d)$$

Where $P_\theta(f,d)$ characterizes the path (without the antenna elements) for a given frequency and distance given the parameter vector $\theta$ (for example $\theta$ may include propagation velocity and path loss), and $A_c(f)$ characterizes the unknown response of the antenna elements for a given configuration, where the same configuration c implies the same antenna polarization relative to path direction (as an example, in FIG. 1B, pairs (1-5)(1-9)(5-9)(1-13)(2-6), etc have one configuration, and pairs (1-6)(1-11)(6-16)(2-12), etc have a second configuration. For the specific case where only time-delay is assumed the following Eq is used:

$$P_\theta(f,d)=e^{-j2\pi f \nu \cdot d}$$

$$Y(f,d,c)=A_c(f)\cdot e^{-j2\pi f \nu \cdot d}$$

It is clear from the equation above that if there are multiple distances d, then $\nu$ can be extracted by finding the peak of the FFT of $Y(f,d)$ taken over the same frequency and different distances. The more general metric below is derived from best-fit of $A_c(f)\cdot P_\theta(f,d)$ to $Y(f,d,c)$:

$$\mu(Y;\theta) = \sum_{f,c} \frac{\left|\sum_d Y(f,d,c)\cdot P_\theta^*(f,d)\cdot w(d)\right|^2}{\sum_d |P_\theta(f,d)|^2 \cdot w(d)}$$

$w(d)$ is an optional weighting function which can be used in order to given higher or lower weight to near/far pairs. The metric is oblivious to frequency dependent but distance-independent phase that can be embedded in $A_c(f)$.

The parameters $\theta$ are estimated by finding the maximum of $\mu(Y;\theta)$.

This algorithm is less computationally intensive than the previous because computations scales like the number of pairs, rather than the number of pair-couples (ref-sig couples).

Estimating Layered Media

According to some embodiments of the invention there is provided a method for estimating a media to obtain the media's properties such as the media's dielectric properties wherein the media is a layered media, for example a two layered media as shown in FIG. 2D or a multilayer media. This estimate may be used for imaging the media. In some cases, the width and the propagation velocity of the layered media may be unknown. In this case, utilizing bi-static measurements of near and far pairs of antennas as will be illustrated below can be used to jointly estimate the two unknowns parameters, in accordance with embodiments of the present invention.

As an example, a single vertical unknown layer (such as layer 274 of FIG. 2D) acts as a mirror. The method for obtaining the medium's unknown parameters include the following steps:

Let $L_p$ be the distance between the antennas in a given antenna pair p, w be in unknown width, and $\nu$ be the unknown propagation velocity in the layer, then the round-trip delay is $$T_p = \frac{2}{\nu}\sqrt{w^2 + \left(\frac{L_p}{2}\right)^2}.$$

The round trip delay is measured from the reflected signals. In order to minimize the effect of other reflectors on the result, averaging of multiple pairs with the same distance, and of various locations is done. Using a simplistic algorithm, from two different delays $T_1$, $T_2$ both $\nu$ and w can be extracted according to the following Eq:

$$\nu = \sqrt{\frac{L_2^2 - L_1^2}{T_2^2 - T_1^2}}, \quad w = \frac{1}{2}\sqrt{\frac{L_2^2 T_1^2 - L_1^2 T_2^2}{T_2^2 - T_1^2}}$$

In another implementation, instead of estimating $T_p$ from the received signals, a best-fit or maximum-likelihood algorithm is employed. For each hypothesis on $\nu,w$, the time delays $T_p$ are calculated. Then, $\nu,w$ can be chosen to maximize the fit metric $S(w,\nu)=|\Sigma_p y_p(T_p)|$, where $y_p(t)$ is the time-domain signal recorded for pair p, and $T_p$ is the hypothesized delay given by the equation above as function of $w,\nu$, and S measures the measure of fit between the received signal and the assumed layer parameters $w,\nu$. The signals may be pre-processed, e.g. by dividing each time-domain signal by an estimated standard deviation (a process referred to as whitening), in order to improve detection performance.

The metric $S(w,\nu)$ may be replaced by other fit metrics that measure the signals alignment. As for example $$S_2(w,\nu) = \max\{\Sigma_p(\max\{y_p(T_p), 0\})^2,$$

$$\Sigma_d(\min\{y_p(T_p), 0\})^2\},$$

$$S_3(w,\nu) = |\hat{a}|\Sigma_p \min\left(\max\left(\frac{y_p(T_p)}{\hat{a}}, 0\right), 1\right) \text{ where}$$

$$\hat{a} = \text{median}(y_p(T_p)) \text{ and}$$

$$S_4(w,\nu) = \max_{q\in\{\pm 1\}} \Sigma_p \max(0, y_p(T_p)\cdot q).$$

In the case of multiple layers this process is repeated iteratively to estimate all layers, while making the necessary adjustments in the equations used for determining $T_p$, to account for propagation times in the layers already estimated and for refractions.

An algorithm to detect multiple layers may include finding multiple peaks in the function $S(w,\nu)$ described above, that exceed a certain threshold. When multiple layers exist in the media, the estimated parameters (peak in $S(w,\nu)$) for each layer represent an average (mixture) of the propagation velocities of all previous layers, an effect which distorts the estimate of propagation velocity for any layer except the first. In the case multiple layers are detected, the estimated widths and velocities in each layer following the first one, are corrected according to the estimated parameters of the previous layers, in order to compensate for the effect of previous layers on the estimate. Suppose there are N layers and the estimated parameters for them, when independently estimated, are $(w_i,\nu_i)$, $i=1, \ldots, N$. Denote the corrected parameters $(\tilde{w}_i,\tilde{\nu}_i)$. These parameter are obtained by requiring that the first estimate $(w_i,\nu_i)$ represents the total depth and total time of this and previous layers: $w_i=\Sigma_{j\leq i}\tilde{w}_j$ and $$\frac{w_i}{\nu_i} = \sum_{j\leq i} \frac{\tilde{w}_i}{\tilde{\nu}_i}$$

and results in the correction formulas: $\tilde{w}_i = w_i - w_{i-1}$ and $$\tilde{v}_i = \frac{w_i - w_{i-1}}{\frac{w_i}{v_i} - \frac{w_{i-1}}{v_{i-1}}} \text{ (for } i > 1\text{)}.$$

In cross-polarized arrays, the ratio between the interface-reflection measured in horizontal and vertical pairs (TM and TE refractions) yields additional information, because it yields the ratio of Fresnel's coefficients. For example, having estimated v, w one can infer the propagation velocity (refractive index) of the medium following the interface. On the other hand, if this medium is known, these measurements yield additional information to validate the assumptions on v or w.

Although the description above focuses on the simple problem of estimating a parallel layer, the same concept—of comparing near and far pairs—may be used to estimate the parameters of any parametric layer or reflector (for example, a layer with periodic structure of varying width, a diagonal or curved layer).

Figure 5:
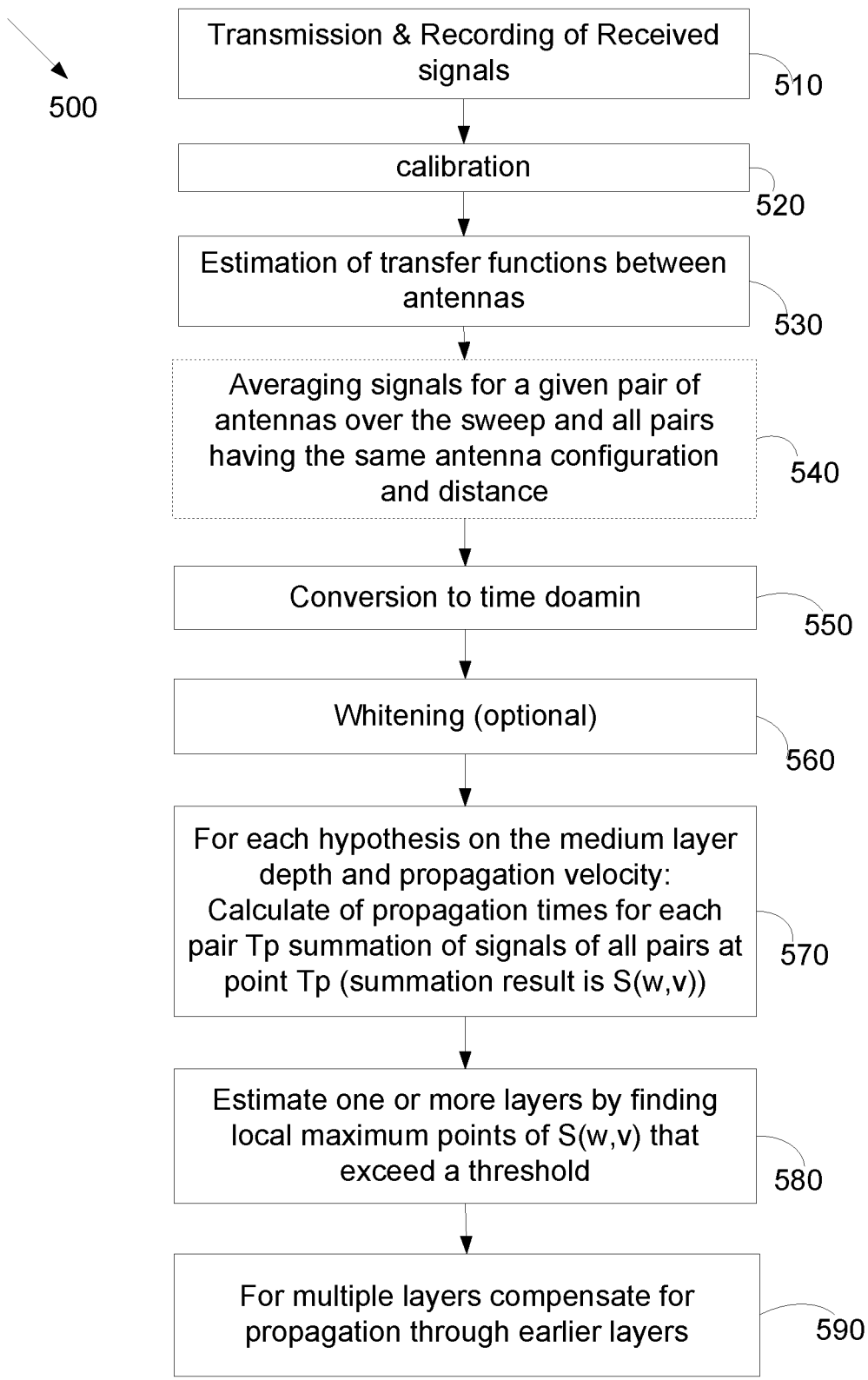
FIG. 5 is a flowchart of a method for estimating media parameters, such as the depth and propagation velocity of a medium wherein the medium is a layered medium, in accordance with embodiments of the invention.

FIG. 5 is a flowchart 500 of a method for estimating media parameters, such as the depth and propagation velocity of a medium, in accordance with embodiments of the invention, wherein the medium is a layered medium, for example a multilayered medium. In some cases the layered medium may be the two layered medium 270 as shown in FIG. 2D. The estimation and measuring process is based on to a plurality of background reflectors (e.g. random reflections), reflected or affected from the media as illustrated in FIG. 2D. At step 510 a plurality of signals are transmitted by an antenna array, such as the antenna array of FIG. 1B. The reflected signals reflected or affected from or by the scattering objects (e.g. irregular objects) within the media are received by the antenna array and are recorded for example by the processor of system 100. At step 520 the system is calibrated. The calibration is performed by the processing unit and includes dividing the signals by reference signals representing the responses of the measurement device, traces, antenna elements and so forth. Following the calibration process the received signals for a given pair of antennas over the sweep and optionally all pairs of antennas having the same antenna configuration and distance are averaged at step 540. For example pairs (1-2), (5-6), (11-12) of the exemplary antenna array of FIG. 1B may be averaged together, and pairs (1-4), (5-8), (9-12), etc. are also averaged together. At step 550 the averaged signals are converted to time domain and optionally at step 560 a whitening process including division of the time-domain signals by estimated standard deviations of the noise and interference is performed on the processed signals. At step 570 a fit metric value (as for example S(w,v) described above) is calculated for each hypothesis on the medium layer depth and propagation velocity. The process includes a calculation of propagation time for each pair of antennas of an antenna array as illustrated in FIG. 8 and summing the signals, for example all the signals of all pair of antennas at point Tp. In step 580 one or more of the medium layers are estimated by finding a local maximum point of the fit metric S(w,v) that exceed a threshold (a fixed number T, e.g. finding peaks that satisfy S(w,v)>T). At step 590 the propagation velocity for each layer of the medium multiple layers is compensated according to previous layers, a process illustrated for the case of two layers by the example above.

Autofocusing Targets by Tracking

According to another embodiment of the invention there is provided a method of autofocusing by e.g. maximizing target strength on the resulting image. Autofocusing an image can be performed by computing the image for several values of the unknown parameters (as for example propagation velocity), and choosing the values of the parameters for which the peak or several strong peaks of the image are maximized. This process is well known in the art but requires computing the image several times. According to embodiments of the present invention the following two methods may be used for autofocusing targets by tracking, without computing the image several times.

According to the first method, following imaging using an a-priori guess of propagation velocity, $v_0$, a set of targets is selected for optimization. These may be, for example, the N strongest points on the image, targets found to be legitimate by comparing to dictionary of targets, or targets selected by the user.

The scan range for velocities is defined as $v \in [v_0 - \Delta_1, v_0 + \Delta_2]$. Scanning this range is done in two stages: in the first stage starting from $v_0$ and decreasing velocity up to $v_0 - \Delta_1$ in steps of $\Delta v$, and in the second stage, starting from $v_0$ and increasing velocity up to $v_0 + \Delta_2$ in steps of $\Delta v$. In each stage, the initial target positions and strengths, are obtained from the initial image, and then updated through the scan.

The change of assumed velocity, changes the locations where the targets would appear (had the image been regenerated). Therefore the location is tracked: after each increase or decrease of the velocity in $\Delta v$, the location of each target is updated to the local maxima found in the vicinity of the previous location. An algorithm to achieve is by calculating the image at for example 8 points or voxels at small distance around the current location (negative or positive shift for any of the 3 axes), and if any of these points yields a stronger value than the original location, move the location to that point and re-iterate, until a convergence is achieved.

Tracking of targets is not only more efficient than regeneration of the image. It also prevents locking on and optimizing the power of false targets.

Another possible implementation is by moving to the direction of the image gradient until the gradient is close to zero, or any other local optimization procedure.

Finally, after the two scans are completed, a target strength for each target and each velocity in the range is known. From this function, the estimated velocity is determined so as to jointly maximize the strength of all targets (a simple metric being the sum of all target strengths, but other metrics may be used as well).

In some cases, a layered media requires performing ray-tracing in order to find the accurate path delays (incorporating snell's law at the interface). A ray tracing process is defined as computation of the ray path from the Tx antenna to the target and back to the Rx antenna (which, in general, is not a straight line). For example the path to the lowest target such as target 281 of FIG. 2D. In this case, after each update of the propagation velocity in one media or the other, the points of incident of the rays on the layer interface (for a given antenna and a given target location) have to be updated so that they satisfy snell's law. Computation of the incident points, especially for general layers, is computationally intensive. In some applications, in which the search range of velocities is small enough, the incident points are not updated during the scan. In other applications, the incident points are tracked while the velocity is gradually changed using a similar process to the one described above.

Autofocusing Targets by Local Ridge Alignment

According to another embodiment of the invention there is provided a method for obtaining parameters of a media such as the media's dielectric parameters and imaging the media and objects or targets within the media comprising autofocusing targets by local ridge alignment. The autofocusing method attempts to maximize the maximum point at each 'region' (other metrics are possible as well), using an approximation methods. The assumption is that only a single strong target may exist in each "region". A 'region' is defined as a small part of the image. The image is arbitrarily broken into multiple regions, where the size of each region (in each dimension) might be a certain multiple of the basic imaging resolution (for example 10 times the imaging resolution).

Figure 6:
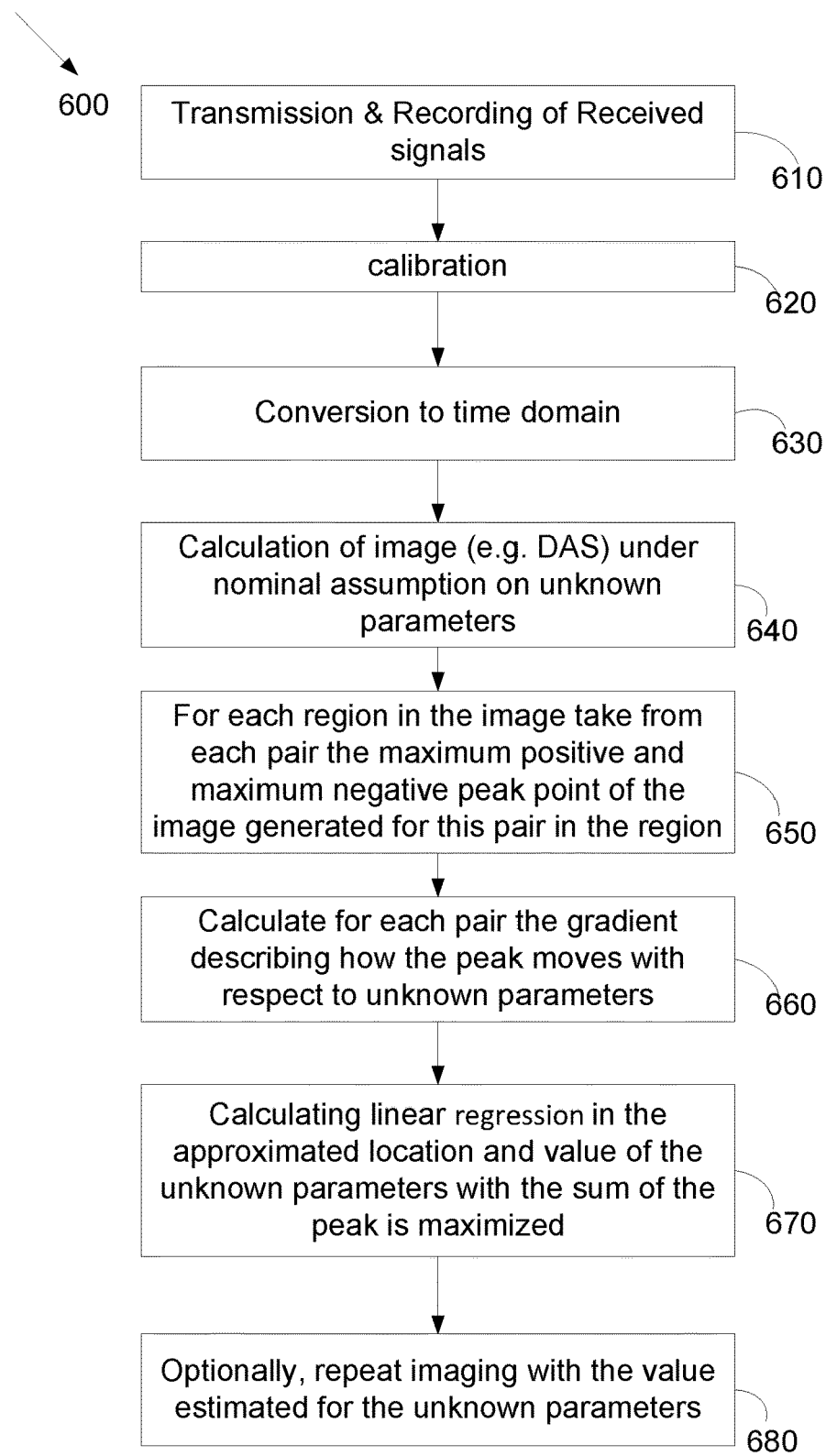
FIG. 6 is a flowchart of a method for autofocusing on selected and specific points or areas of the media by utilizing a ridge alignment process, in accordance with embodiments of the invention.

FIG. 6 is a flowchart of 600 a method for autofocusing by a system such as the system of FIG. 1A on selected and specific points or areas of the media image by utilizing a ridge alignment process, in accordance with embodiments of the invention;

At step 610 a plurality of signals are transmitted by an antenna array, such as the antenna array of FIG. 1B. The reflected or affected signals reflected or affected from or by the scattering objects within the media are received by the antenna array and are recorded for example by the processor of system 100. At step 620 the system is calibrated. The calibration is performed by the processing unit and includes dividing the signals by reference signals representing the responses of the measurement device, traces, antenna elements and so forth. Following the calibration process the received signals may be converted to time domain at step 630. At step 640 the image of the medium is processed according to nominal assumptions in regard to unknown parameters of the media as will be followed accordingly in regard to steps 650-680. At step 650 for each region of the image, for example in a size of between 1 and ×10 times the image resolution, for each pair of antennas, the maximum positive and maximum negative peak are obtained. At step 660 a small-deviation model for the peak location is obtained by calculating a gradient for each pair of antennas. The gradient describes how the peak of the pair of antennas moves with respect to unknown parameters of the medium (e.g. velocity and depth). At step 670 a linear regression of the approximated location of the media is calculated. Additionally the value of the unknown media parameters and the sum of peaks as calculated at step 660 are maximized according to maximizing algorithms as known in the art. Optionally in step 680 the imaging step are repeated according to the unknown parameters estimated value as obtained at steps 640-670.

In many cases, including particularly all linear imaging algorithms (for example DAS, or any image which is a linear function of the signals), the image can be thought of as a sum of images obtained by different pairs. As an example the DAS image $I_{DAS}(r)=\Sigma_p y_p(T_p(r))$ can be thought of as a sum of pairwise images $I_p(r)=y_p(T_p(r))$.

For each antenna pair, the image is approximately constant along a certain manifold, for example an ellipsoid (representing fixed delay), and the ellipsoid or manifold can be locally approximated by a plane. The purpose now is to find the value of the propagation velocity that will maximally align these planes so that ideally they all intersect at one point and maximize the image value.

When the velocity is slightly changed, the same signal value will be associated with a slightly different point in space, and therefore the image associated with the specific pair will shift slightly. The images for different pairs move in different directions, and hence a parameter that best aligns them can be found.

Figure 9:
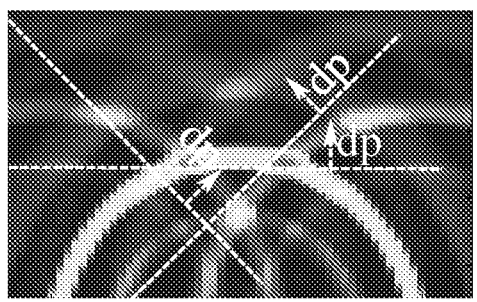
FIGS. 9-10 illustrate a simulation of a imaging at different medium velocity, in accordance with embodiments of the invention.
Figure 10:
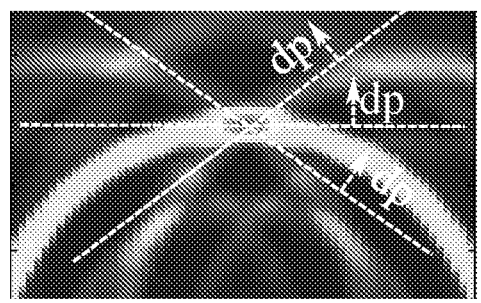

FIGS. 9 and 10 illustrate an image of a ball using 3 pairs of antennas and demonstrating the ridges, i.e. the surfaces representing in a way of approximation the contribution of each antenna pair to the image near the target location, together with the actual contribution of each pair to the image, which appears like a set of ellipses. In FIG. 9 the target is not focused and the ridges are not aligned and in FIG. 10 the target is in focus and ridges are aligned.

The autofocusing method includes the following steps, in accordance with embodiments of the present invention:

1. Take from each pair the maximum positive and maximum negative peak point of the image generated for this pair of antennas in the region. An area larger by a prescribed extend than the region is searched, because the fact the peak is in the region doesn't mean each pair's peak is in the region.
2. Take the amplitude $A_p$ (where p is the pair number), original peak location $r_p$ (in a 3 dimensional axis system) and direction of propagation $d_p$ (=the direction in which the image for that pair has the maximum change, and is orthogonal to the "ridge" or ellipse direction).
3. Potentially, the curvature at the peak (dependent on the bandwidth) can be captured and used as well, however a good simplifying assumption is that all signals have the same curvature.
4. With each we associate a gradient $g_p$. If the propagation velocity is changed to $v=(1+\alpha)v_0$ then the ridge moves in the original direction of propagation a distance of $\alpha \cdot g_p$.
5. The gradient is computed using the distances travelled from the antennas to the target in the medium of interest. It is possible that the path between the antenna and the target is composed of several media. If only one media has unknown velocity then only the propagation length in that media should be accounted for.

A possible approximate expression for the gradient is $$\frac{L}{\|d_T+d_R\|}$$

where L is the total path distance in the media of interest and $d_T$, $d_R$ are the directions of arrival and departure from the point $r_p$ in space to the TX and RX antennas. This implies that if the propagation velocity is changed to $v=(1+\alpha)v_0$ then the ridge moves in the original direction of propagation, a distance of approximately $$\alpha \frac{L}{\|d_T+d_R\|}.$$

For example, for the monostatic case $d_T=d_R$, the gradient is $$\frac{L}{\|d_T+d_T\|}=\frac{L}{2},$$

which is the one-way distance.

6. In one application:
   The parameter $\alpha$ that best aligns the ridges is computed. For example, under L2 norm (or equivalently for optimization of the image peak) the value of the parameter is:

$$\hat{\alpha} = \left( \sum_p A_p \cdot \begin{bmatrix} d_p d_p^T & d_p g_p \\ d_p^T g_p & g_p^2 \end{bmatrix} + \lambda I \right)^{-1} \sum_p g_p A_p (r_p^T d_p)$$

Where $\lambda$ is a small diagonal loading factor.
   The process is repeated for positive and negative peaks and take the result that yields the strongest peak is taken (for each region).
   The results $\hat{\alpha}$ of all regions, using a weight function taking into account the original amplitudes $A = \Sigma_p A_p$, or the amplitudes after alignment. $\hat{\alpha} = \Sigma_{region} \hat{\alpha}_{region} \cdot w$ ($A_{region}$).
7. In another application the optimum image point per region is found as a function of $\alpha$ (under the approximation), and then a is found by maximizing an image-level criterion.
   For each region, $I(\alpha)$ is the approximate image-peak per value of $\alpha$ per each region, is given by the expressions in the following Eq.
   At the image level the best $\alpha$ for all regions simultaneously is found, by optimizing a global metric. For example the maximum image, the average power, the average over the strongest N peaks, L(p)-norm, median, etc.

---

The approximate maximum image strength in a region as function of $\alpha$ is given by the following Eq:
$$I(\alpha) = I_0 - 2\beta D_1 \alpha - D_2 \beta \alpha^2$$
Where $$I_0 = \sum_p A_p$$

$D_1 = F(y_0, g)$
$D_2 = F(g, g)$
F (a, b) is defined for two vectors a, b as $$F(a, b) \stackrel{def}{=} \sum_p a_p A_p b_p - \left( \sum_p d_p A_p a_p \right)^T \left( \sum_p d_p A_p d_p^T + \lambda I \right)^{-1} \left( \sum_p d_p A_p b_p \right)$$

And $\beta$ is a constant curvature assumed for the waveform $\left( \text{typical value is } \sqrt{\frac{8}{\lambda}} \text{ where } \lambda \text{ is the wavelength} \right.$

---

In layered media because the delay from the antenna to the target depends, in general, on the propagation velocities in all layers, this optimization is performed using several unknown variables, being the propagation velocities in all the media up to the relevant point in space.

The same algorithm can be applied to compensate for other factors effecting target focus, for example, target radius, antenna response, and so on. This is done by replacing the gradient parameter g by the suitable gradient describing the dependence on the required parameter. The method is easily extended to deal with several unknown parameters.

Ridge Alignment for Scans Over Multiple Locations

According to another embodiment of the invention there is provided a method for obtaining parameters of a media such as the media's dielectric parameters and imaging the media and objects or targets within the media comprising a step of ridge alignment for multi-location scans. For such scans, measurements are gathered from the array placed in different locations (either using a full array or one antenna/pair), and there is no sufficient resolution in a single image in order to estimate propagation velocity. Even if the target can be localized from a single snapshot (location), the resolution improves as more locations are aggregated and as a result the accuracy of velocity estimation has to be improved as well in order to obtain focused image.

In this case, the ridge-alignment method offers significant simplification over focusing at the image or signal level, because the original signals do not have to be stored. The 4 sums in the expression for F(a, b) (for example, $\Sigma_p d_p A_p b_p$), which are sums over pairs, are aggregated from location to another, where each location adds more pairs. I.e. after recording the signals at each location, adding to the sums in the expression, the contribution of the pairs recorded at the current location. The result of each such process is a list of regions and the accumulated sums of each of the regions. In the next location, overlapping regions are identified (i.e. having same or similar absolute locations), the ridge parameters ($A_p$, $d_p$, $g_p$) are identified for them, and the result is accumulated to each of the sums (the additional snapshot is treated as additional antenna pairs).

Then, after recording at each location, the estimation of velocity correction follows as previously: the function $I(\alpha)$ for each of the regions is evaluated as function of $\alpha$, and a global metric is applied to select the best $\alpha$.

Medium Estimation Based on Extrinsic Measurements

According to another embodiment of the invention there is provided a method for obtaining parameters of a media such as the media's dielectric parameters, which may be used for imaging the media and objects or targets within the media, comprising performing extrinsic measurements on the medium. An extrinsic measurement in accordance with embodiments of the invention is defined as a measurement not obtained by the antenna array used for imaging, or by a measurement performed on the antenna array used for imaging but does not measure reflections from the media (for example, measuring capacitance through the antenna ports). The extrinsic measurement method may be used in order to supply additional or supporting information, or give a starting point for autofocusing. Especially in scanning applications where the image is gradually built over multiple locations, it is important to have an initial value for the propagation velocity before imaging starts.

A method for estimating the low-frequency dielectric constant $\epsilon_R$, using an array of fringe-capacitors is presented. While fringe-capacitors are known art, the proposed design is aimed at sensing the medium at different depths in order to generate an estimate of the dielectric constant per depth. Dielectric sensing by means of capacitive sensing is established in the art. Typically, a transmission line will be open ended, portraying a capacitance which depends on the dielectric properties in the vicinity of the (fringe) electric field. The methods described below are based on one or more sensors, wherein each sensor is comprised of one or two conductive elements, whose geometrical shape determines their sensitivity to various parameters of the medium.

Differentiating Structures within a Medium

In some cases, a single dielectric sensor does not have the capability of differentiating unambiguously between different structures within the volume of integration (fields effective volume) of a medium. This volume of integration is roughly proportional to the lateral extent of the capacitor.

By employing several dielectric sensors of different lateral dimensions, one can acquire the dielectric properties over (overlapping) volumes.

Figure 11A:
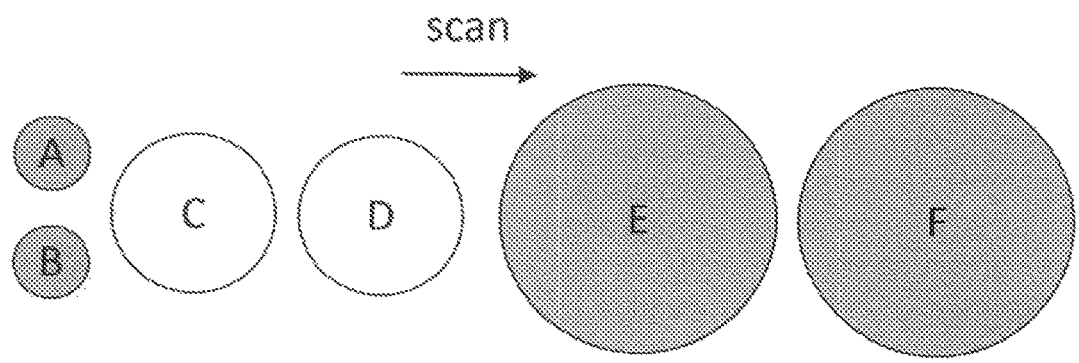
FIG. 11 illustrates different capacity sensors, in accordance with embodiments of the present invention.
Figure 11B:
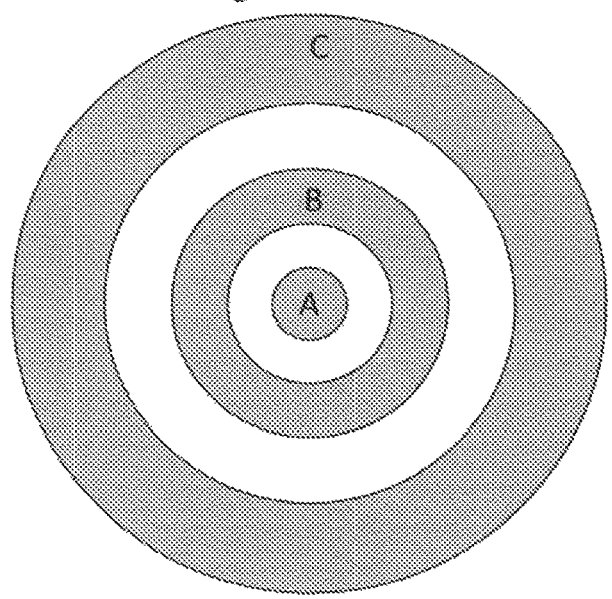
Figure 11C:
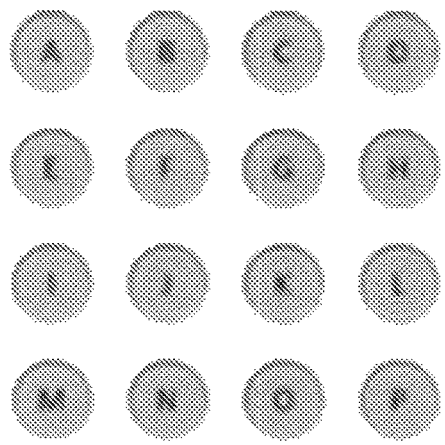

It is then possible to spatially resolve dielectric properties in a resolution which is limited primarily by the granularity of the lateral difference between the sensors. Evaluating a given area may be done by translating different sensors as shown for example in FIG. 11. For example FIG. 11 illustrate different capacity sensors in accordance with embodiments of the present invention. FIG. 11A illustrates a number of capacitive sensors A-F of various size. For example in a size of between 1 mm and 5 cm. A concentric capacitive sensor 1200 is illustrated in FIG. 11B, and capacitive array comprising capacitive sensors A-P is illustrated in FIG. 11C. Example of capacitive sensors may be for example capacitive sensors as illustrated by the present applicant PCT application number PCT/IL2015/050099 entitled "SENSORS FOR A PORTABLE DEVICE".

Figure 12:
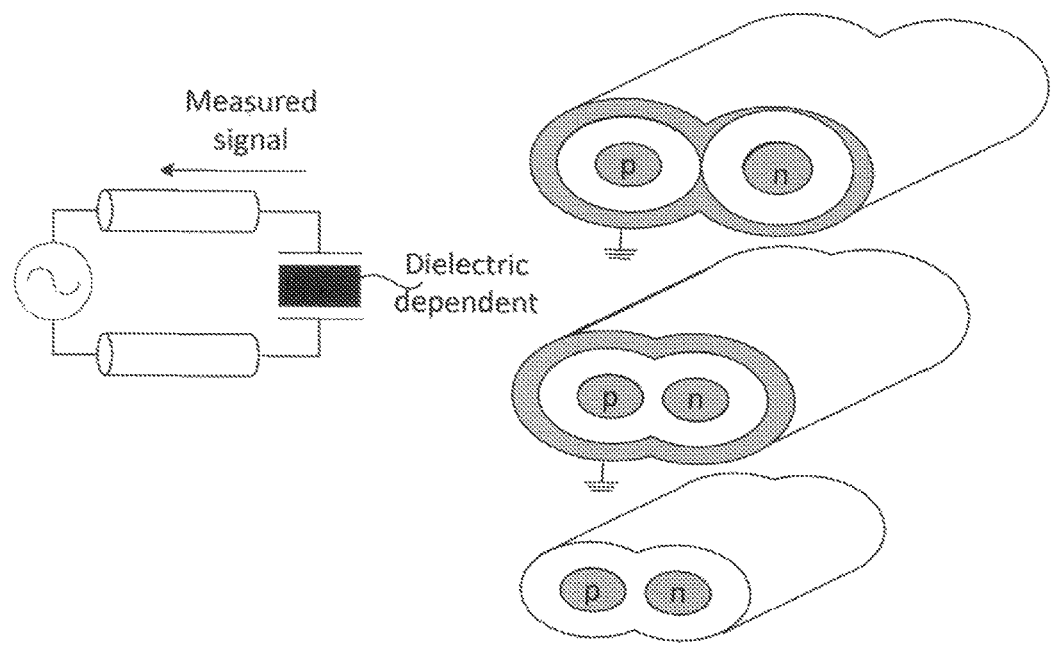
FIG. 12 illustrates a differential capacity measurement, in accordance with embodiments of the present invention.

In some cases the capacitive sensors, such as the capacitive sensors of FIG. 12 may be integrated or add to the antenna array such as the antenna array of FIG. 2.

Differential Measurement

In some cases, the measurement process of the present invention to obtain the properties of the medium or the object may further include differential measurements. Differential measurement may be defined as a voltage or current introduced to the two elements of which the sensor is comprised with inverse signs, and respectively the received signals are obtained by subtracting the voltage or current from two elements from which the receiving sensor is comprised.

Figure 14:
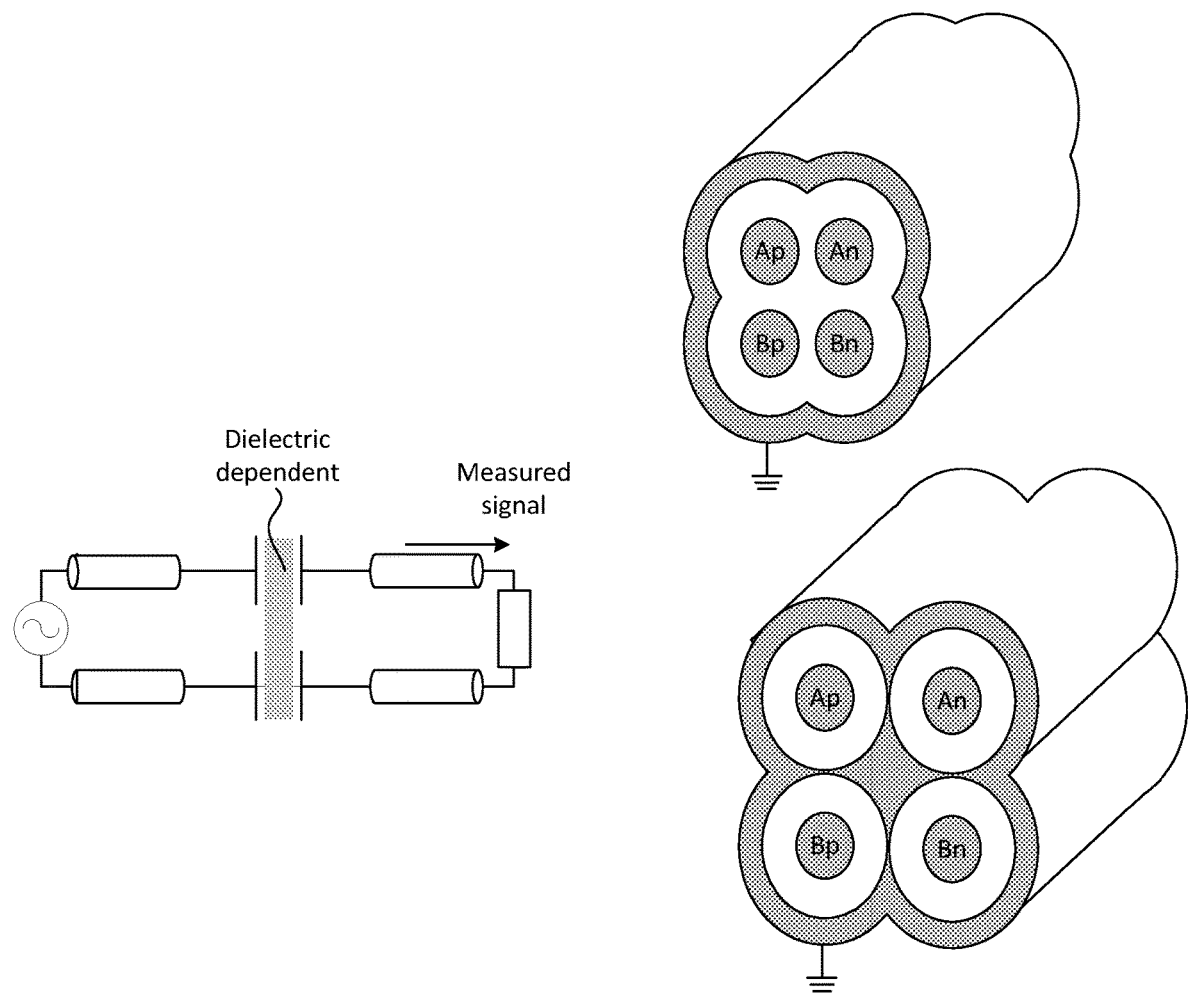

While typically capacitive dielectric sensors measure differences in the reflected single ended signal due to an effective capacitive load, one may implement a reflection measurement in a differential stimulus by utilizing one of the sensors as illustrated in FIG. 14. This holds the benefits of:

shielding the measured signal from disturbances
allowing measurements where a common mode may otherwise affect the measurement Transmissive Measurement In some cases, the measurement process of the present invention to obtain the properties of the medium or the object may further include a transmissive measurement. Typically capacitive dielectric sensors measure differences in the reflected signal due to an effective capacitive load, a transmissive measurement holds several benefits. Amongst said benefits is an increase in dynamic range, as the measured signal is only the (weak) coupling between capacitive ports, as opposed to the large return signal which is only weakly perturbed by the capacitance change.

Figure 13:
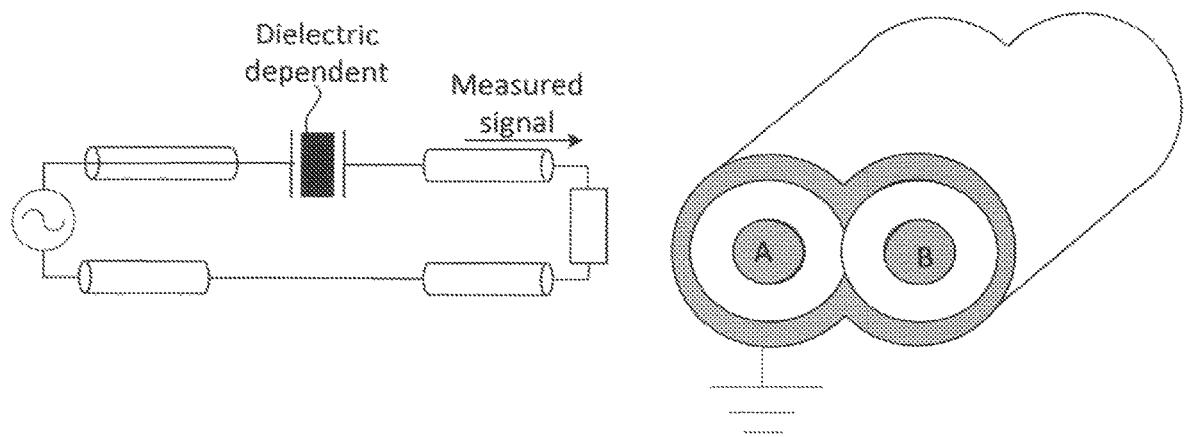
FIGS. 13-14 illustrate differential transmissive measurements, in accordance with embodiments of the present invention.

Such a transmissive arrangement may be implemented by measuring either in single ended or differential modes the capacitance between two ports (A, B). Single ended configuration is shown in reference to FIG. 12. A differential configuration is shown in reference to FIG. 13.

Combination of Information from Antennas with Other Modalities

In some cases, the measurement process of the present invention to obtain the properties of the medium or the object may be further combined with information, received from other antennas, sensors or modules.

Fringe capacitors allow direct measurement of $\epsilon_R$. Other modalities may supply indirect information, that, when combined with information obtained via the antennas/sensors used for imaging, of the invention can yield an estimate of $\epsilon_R$, or other media properties. In some cases, the depth of a metal target is estimated using inductive measurements (e.g. measurements evaluating the change of inductivity of a coil in presence of the target). This information is combined with the time-of-arrival information measured via the antennas, to produce an estimate of average propagation velocity in the depth layers up to the target.

Magnetic means of depth estimation of a metallic object is dependent primarily on permeability, and not on permittivity. Thus, by estimation of the depth of a metallic (or otherwise conductive) target by magnetic means one can tune a 'focusing' algorithm so that the target depth coincides.

This may be further broadened by noting that targets at different depths may be utilized to find the dielectric permittivity profile (and not merely an average figure). Similarly, the present invention methods and systems, may be used in conjunction with varied angular paths—as may be especially useful in the case of relatively well layered media. Finally this method may conceptually be utilized as a measure of inhomogenity.

Figure 15:
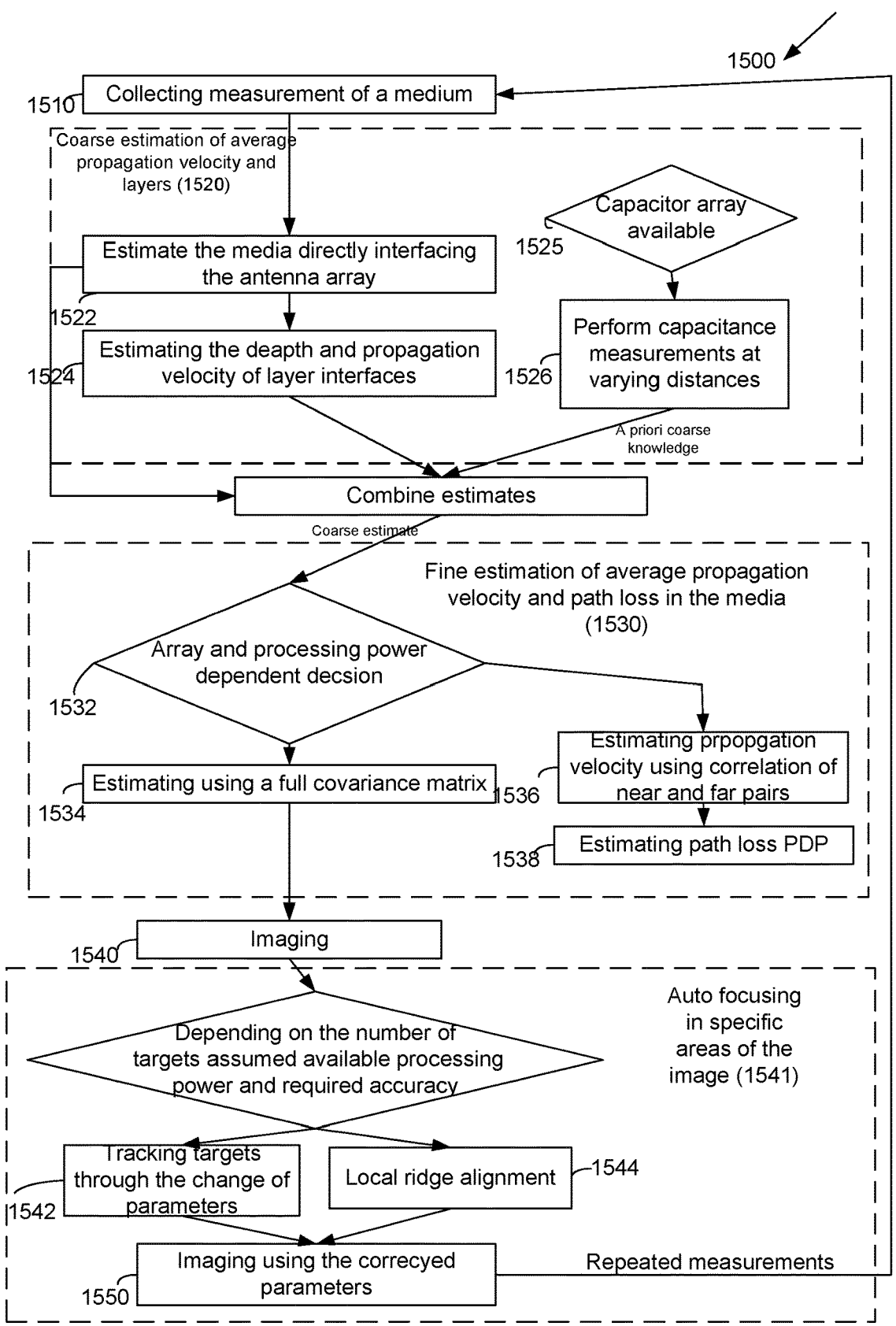
FIG. 15 illustrates a flow chart of combination of various measuring methods and devices comprising various types of sensing devices, such as antennas array and capacitive sensors, to obtain the properties of a medium and objects within the medium in accordance with embodiments of the present invention.

Reference is now made to FIG. 15 illustrating a flow chart 1500 of combination of various measuring methods and devices comprising various types of sensing devices, such as antennas array and capacitive sensors, to obtain the properties of a medium and objects within the medium in accordance with embodiments of the present invention.

Some steps of method 1500 may be carried out at least partially by at least one computer processor, e.g., by processor 109. Respective computer program products may be provided, which comprise a computer readable storage medium having computer readable program embodied therewith and configured to carry out of the relevant stages of method 1500. The measuring process includes a first baseline estimation 1505 which includes the following steps: In step 1510 the measurements of signals transmitted and received by the antenna array, such as the antenna array 210 illustrated in FIG. 2 is obtained by at least one of the processing units.

In step 1520 an average propagation velocity and layers of the medium are estimated for example by a coarse estimation followed by a fine estimation step 1530 of average propagation velocity and path loss in the media to obtain these parameters for the layers of the media.

It is stressed that the media layers detected in the first stage 1505 are used as baseline to produce ray paths (as explained above referring to ray tracing). The propagation velocity detected in first stage is used to determine a search range for propagation velocity in the fine algorithm.

In step 1540 the substance or the medium are imaged using the average parameters detected in step 1530. In step 1550 specific areas of the image such as areas where the starting point is the average parameters detected above are autofocused in accordance with methods known in the art.

The purpose of autofocusing step is to improve the accuracy of unknown media parameters such as EpsR and to provide a solution for scenarios where the parameters are different in parts of the arena (e.g. the propagation velocity and path loss change between the first and the last location, or between depth layers). In this case the previous methods mentioned estimate the average parameters while autofocus may improve the estimation of the parameters in specific parts of the image.

The process is finalized in step 1550 and the media and objects within the media are imaged according to the corrected parameters as obtained by the pervious steps (steps 1510-1550).

According to some embodiments of the invention the step of collecting measurements may be done before processing or interleaved with the processing and/or imaging stages. For example, following collecting part of the measurements, an initial estimation of the medium parameters may be performed, and a partial image may be calculated. In parallel, new measurements may be obtained and the data from these measurements is combined to improve the estimations and/or image new parts of the object.

In some cases the the stages illustrated above (e.g. steps 1510-1550) may include the following sub-steps implemented by the methods described herein:

Step 1520: Coarse Estimation of Average Propagation Velocity and Layers

The purpose of step 1520 is to provide a rough estimation of propagation velocity and layers in the media. Depending on the system type, step 1520 may be bypassed if a rough value for propagation velocity is known a-priori (e.g. an average propagation velocity in breast cancer detection may be known).

In some cases step 1520 may be followed by step 1522. At step 1522 the media interfacing the antenna array is estimated directly as will be further illustrated below by the "estimation of directly interfacing media" method. At step 1524 if a strong reflection from a layer in the media is detected, the measuring process includes estimating the depth and propagation velocity of layer interfaces.

According to some embodiments the system may include one or more capacitive sensors or a capacitor array. In some cases an external capacitive sensor or array may be used to scan the medium. Alternatively or additionally, one or more of the sensors of the system's sensors are capacitive sensors.

If the system includes a capacitive sensor (step 1525) a capacitance measurements may be performed in step 1526 at varying distances from the medium. For example 1, 2, 3, 4, 5, 6, 7, 8, 9, 10 mm or more from the medium. The capacitance measurement may be performed a number of times from varying distances from the medium. The capacitance measurement may be performed according to a method as will be illustrated below entitled
Medium Estimation Based on Extrinsic Measurements In some cases the capacitance measurement of step 1526 may be utilized to validate previous measurements as preformed in steps 1520 and 1530.

Step 1530: Fine Estimation of Average Propagation Velocity and Path Loss in the Media Depending on the available antenna pairs of the array and the available processing power (step 1532) step 1530 includes the following sub-steps for fine estimation of average propagation velocity and path loss in the media. In step 1534 all the media's parameters, (e.g. propagation velocity and path loss) are estimated. In some cases step 1534 is performed by a full covariance matrix as will be illustrated below in the section entitled "estimation by comparison to a covariance matrix"].

In some cases, the parameters such as the propagation velocity are estimated in step 336 using correlations of near and far pairs as illustrated below in section entitled "utilizing correlations of near and far pairs".

In some cases, the parameters, such as the medium path loss may be estimated in step 338 by a power-delay profile (PDP) algorithm as will be further illustrated below in section entitled" estimating path loss by power-delay profile (PDP) below.

Step 1541: Autofocusing in Specific Areas of the Image

Following the imaging step 1540 autofocusing in specific areas of the image according to FIG. 15 is performed in step 1541. It is stressed that either tracking targets algorithm (step 1542) or local ridge alignment (1544) can be used, depending on the number of detected targets, the system available processing power, and required accuracy.

According to some embodiments the autofocus step 1540 is performed by tracking each target through the change of media parameters (step 1542) as will be further illustrated below in regard to section "Autofocusing targets by tracking". Alternatively or additionally the autofocus step may be performed according to local ridge alignment as will be further illustrated in section entitled "autofocusing targets by local ridge alignment".

It is stressed that although step 1540 provides high performant it requires more processing power.

The methods and apparatus disclosed herein can be incorporated with components from antennas systems known in the art, such as systems described in U.S. Pat. Nos. 8,284, 401, 7,236,243, U.S. Publication No. 2015/0036138, U.S. Pat. No. 9,060,113, and U.S. Publication No. 2014/0061486, the entire disclosures of which are incorporated herein by reference [please add any other reference you think should be included].

In further embodiments, the processing unit may be a digital processing device including one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

In some embodiments, the system disclosed herein includes one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device.

In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media. In some embodiments, the system disclosed herein includes at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

In some embodiments, the system disclosed herein includes software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the system disclosed herein includes one or more databases, or use of the same. In view of the disclosure provided herein, those of skill in the art will recognize that many databases are suitable for storage and retrieval of information as described herein. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for measuring parameters of a medium, the system comprising:
   an array, the array comprises at least two transducers, wherein at least one of said at least two transducers is configured to transmit a signal towards said medium, and at least one transceiver attached to said at least two transducers, the at least one transceiver is configured to transmit at least one signal toward the medium and receive a plurality of signals affected by the medium;

a data acquisition unit configured to receive and store said affected plurality of signals; and at least one processor unit, said at least one processor unit is configured to:

(a) process said affected plurality of signals to yield a plurality of transfer functions wherein each of said plurality of transfer functions comprising said medium response between two transducers of said at least two transducers as function of frequency or time;

(b) process said plurality of transfer functions to yield a plurality of statistical measures, wherein each of said statistical measures, is calculated from at least two transfer functions of said plurality of transfer functions; and (c) process said statistical measures to calculate said medium parameters, wherein each of said plurality of statistical measures is calculated from at least one pair of said plurality of transfer functions by multiplying a scalar function of a first transfer function by a scalar function of a second transfer function, and averaging the result of said multiplication over multiple pairs of transfer functions.

2. The system of claim 1, wherein the parameters are selected from the group comprising of:

a propagation velocity, dielectric constant ($\varepsilon_R$), refraction index (n).

3. The system of claim 1, wherein each statistical measure of said plurality of statistical measures is an empirical covariance ($\Lambda_y$) of pairs of said transfer functions, wherein each transfer function of said at least two transfer functions is represented as a vector of samples, and the covariance between two vectors of samples is calculated over a plurality of pairs of said transfer functions having the same configuration.

4. The system of claim 3, comprising:

(a) providing a model, the model comprises a theoretical covariance matrix ($\Lambda_\theta$) for every value of the medium parameters $\theta$, (b) comparing said theoretical covariance matrix to an empirical covariance matrix produced from the plurality of signals, using a comparison metric $\mu$, and (c) selecting a value of the parameters $\theta$ that maximizes a comparison metric $\mu$ ($\Lambda_\theta$, $\Lambda_y$) as an estimate of the medium parameters $\theta$.

5. The system of claim 4, wherein the comparison metric $\mu(\Lambda_\theta, \Lambda_y)$ is selected from the group comprising of:

$$\mu_1(y;\theta)=c(\theta)\cdot tr(\Lambda_\theta,\Lambda_y), \mu_2(y;\theta)=c(\theta)\cdot tr(\Lambda_\theta^{-1},\Lambda_y), \mu_3(y;\theta)=c(\theta)\cdot tr((\Lambda_\theta+\lambda I)^{-1}\Lambda_y),$$

wherein $c(\theta)$ is a normalization function independent of the measurements y.

6. The system of claim 3, wherein the empirical covariance matrix is normalized before integrating the empirical covariance matrix.

7. The system of claim 6, wherein the normalization comprises dividing each element (i, j) in the covariance matrix by the square root of the product of elements (i, i) and (j,j).

8. The system of claim 6, wherein integrating the empirical covariance matrix is performed separately over distinct ranges of times or distances of said medium, said distinct ranges are defined by at least one section of the tangent lines, to produce an estimate of propagation velocity per a distinct range of depths in the medium.

* * * * *